(12) United States Patent
Taguchi

(10) Patent No.: US 9,078,611 B2
(45) Date of Patent: Jul. 14, 2015

(54) CLAMP AND BLOOD COLLECTING DEVICE

(75) Inventor: Noboru Taguchi, Ashigarakamigun (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 1017 days.

(21) Appl. No.: 13/147,322

(22) PCT Filed: Jan. 7, 2010

(86) PCT No.: PCT/JP2010/050114
§ 371 (c)(1),
(2), (4) Date: Aug. 1, 2011

(87) PCT Pub. No.: WO2010/087216
PCT Pub. Date: Aug. 5, 2010

(65) Prior Publication Data
US 2011/0288441 A1    Nov. 24, 2011

(30) Foreign Application Priority Data

Feb. 2, 2009 (JP) .................................. 2009-021566
Feb. 9, 2009 (JP) .................................. 2009-027929

(51) Int. Cl.
*A61B 5/15* (2006.01)
*A61B 10/00* (2006.01)

(52) U.S. Cl.
CPC ............ *A61B 5/15* (2013.01); *A61B 5/150366* (2013.01); *A61B 10/0051* (2013.01)

(58) Field of Classification Search
CPC ............ A61B 5/07; A61B 5/073; A61B 5/15; A61B 5/150366; A61B 10/0051; A61B 10/0048; A61M 5/141; A61M 5/16877
USPC ............ 600/573, 575–577, 579, 580; 604/32, 604/248, 256
See application file for complete search history.

(56) References Cited

U.S. PATENT DOCUMENTS 6,589,197 B1 * 7/2003 Doi et al. ........................ 604/6.1
6,626,884 B1    9/2003 Dillon et al.
(Continued)

FOREIGN PATENT DOCUMENTS

FR    2 153 360 A1    5/1973
GB    1402742    8/1975
(Continued)

OTHER PUBLICATIONS

International Search Report (PCT/ISA/210) issued on Feb. 16, 2010, by Japanese Patent Office as the International Searching Authority for International Application No. PCT/JP2010/050114.
(Continued)

*Primary Examiner* — Max Hindenburg
(74) *Attorney, Agent, or Firm* — Buchanan Ingersoll & Rooney P.C.

(57) ABSTRACT

A clamp is provided in a blood collecting device that includes a first tube having one end and another end connected to a blood collecting needle and a blood bag, respectively, a second tube branched from a halfway of the first tube through a branched portion, and a block-off member which is provided in the first tube at the blood-bag side beyond the branched portion and which allows the first tube in a blocked state to be opened when torn, in which the clamp is arranged at the branched portion, and is configured to change a state between a first state in which the second tube is opened and a tearing operation of the block-off member is disabled and a second state in which the second tube is closed and a tearing operation to the block-off member is enabled.

17 Claims, 20 Drawing Sheets

(56) References Cited

U.S. PATENT DOCUMENTS

| | | | |
|---|---|---|---|
| 7,175,612 B2 * | 2/2007 | Felix et al. | 604/323 |
| 7,824,612 B2 * | 11/2010 | Fuisz et al. | 422/62 |
| 2007/0287953 A1 | 12/2007 | Ziv et al. | |
| 2010/0185159 A1 | 7/2010 | Bagwell et al. | |

FOREIGN PATENT DOCUMENTS

| | | |
|---|---|---|
| JP | 2002-528159 A | 9/2002 |
| JP | 2008-511371 A | 4/2008 |
| JP | 2008-178553 A | 8/2008 |
| WO | 2008/089985 A1 | 7/2008 |
| WO | 2010/084434 A2 | 7/2010 |

OTHER PUBLICATIONS

Extended European Search Report dated Oct. 10, 2012, issued by the European Patent Office in corresponding European Patent Application No. 10735686.7 - 2404/ 2392367. (5 pages).

* cited by examiner

CLAMP AND BLOOD COLLECTING DEVICE

TECHNICAL FIELD

The present invention relates to a clamp and a blood collecting device.

BACKGROUND ART

In order to collect blood, in general, a blood collecting device is used which collects blood into a blood bag (a blood collecting bag) from a blood collecting needle through a tube. The blood collecting device (a blood collecting instrument) disclosed in, for example, Patent Literature 1 is a conventionally known blood collecting device of this type.

The blood collecting device disclosed in Patent Literature 1 includes a blood collecting needle, a blood collecting bag (a bag set) storing blood collected through the blood collecting needle, a blood collecting tube (a first tube) that interconnects the blood collecting needle and the blood collecting bag together, a branched tube (a second tube) branched from the halfway of the blood collecting tube, an initially flowing out blood bag (inspection blood bag (sample porch)) communicated with the blood collecting tube through the branched tube, and a three-way cock (a valve). According to this blood collecting device, since blood may be possibly contaminated by bacteria in or under a skin, an initial flow of blood (initially flowing out blood) collected from a donor is collected (stored) in the initial blood flow bag before blood is collected from the donor (blood donor) in the blood collecting bag, i.e., before a real blood collection is performed. The collected initially flowing out blood is taken in a plurality of blood collection tubes and used for various inspections.

According to such a blood collecting device, the three-way cock can take following three states.

That is, a first state is that the upstream side of the blood collecting tube is communicated with the branched tube (see FIG. 2(a) of Patent Literature 1).

A second state is that the upstream side of the blood collecting tube is discontinued to the branched tube, and the upstream side of the blood collecting tube is communicated with the downstream side thereof (see FIG. 2(b) in Patent Literature 1).

A third state is that the upstream side of the blood collecting tube is discontinued to the downstream side thereof (see FIG. 2(c) of Patent Literature 1).

When the blood collecting device disclosed in Patent Literature 1 is used, first, the three-way cock is set to be in the first state, and in this state, initially flowing out blood is collected into the initially flowing out blood bag. Next, after the initial flow of blood (initially flowing out blood) is collected in the initially flowing out blood bag, the cock (knob) of the three-way cock is operated in order to have the three-way cock become in the second state, and in this state, a real blood collection is carried out. After the real blood collection, the cock of the three-way cock is operated and the three-way cock is caused to be in the third state.

As explained above, according to the blood collecting device of Patent Literature 1, when a process transitions to a real blood collection after the initially flowing out blood is collected, the upstream side of the blood collecting tube is discontinued to the branch tube, and the upstream side of the blood collecting tube is communicated with the downstream side thereof (the three-way cock is caused to be in the second state).

According to the blood collecting device of Patent Literature 1, however, it is not easy to figure out in which state from the first to third states the three-way cock is, so that, for example, at the time of collecting an initially flowing out blood in the initially flowing out blood bag, if the three-way cock is not in the first state and is already in the second state due to an artificial error (i.e., unintentionally), when it is not figured out and an initially flowing out blood is collected, the anticoagulant in the blood collecting bag is mixed in the initially flowing out blood, and the precision of inspection thereafter decreases. Also, since the initially flowing out blood does not enter the initially flowing out blood bag but enters the blood collecting bag, there is a possibility that blood used for blood transfusion is contaminated by bacteria. As explained above, according to the blood collecting device of Patent Literature 1, after the initially flowing out blood is collected, when a process is transitioned to a real blood collection with the three-way cock being in the second state, the three-way cock can be in the second state before such a transition, i.e., before the upstream side of the blood collecting tube is discontinued to the branch tube, the upstream side of the blood collecting tube may be communicated with the downstream side thereof, resulting in a difficulty of carrying out a correct operation mentioned above.

Patent Literature 1: Japan Patent Publication No. 2002-528159

DISCLOSURE OF INVENTION

It is an object of the present invention to provide a clamp and a blood collecting device which can surely prevent a first tube from being opened before blocking a second tube branched from the first tube in the blood collecting device when such blood collecting device is operated.

In order to achieve the above object, the present invention provides a clamp which is provided in a blood collecting device that includes: a first tube having one end and another end connected to a blood collecting needle and a blood bag, respectively; a second tube branched from a halfway of the first tube through a branched portion; and a block-off member which is provided in the first tube at the blood-bag side beyond the branched portion and which allows the first tube in a blocked state to be opened when torn, in which the clamp is arranged at the branched portion, and is configured to change a state between: a first state in which the second tube is opened and a tearing operation to the block-off member is disabled; and a second state in which the second tube is closed and a tearing operation to the block-off member is enabled.

Accordingly, it is possible to prevent the first tube from being opened without fail before the second tube branched from the first tube in the blood collecting device is closed when the blood collecting device is operated.

It is preferable that the clamp of the present invention should include a clamp main body and an operation member rotatable relative to the clamp main body, the operation member should include a pressing portion that presses and closes the second tube and a preventing portion that prevents a tearing operation to the block-off member, and when the operation member is operated to rotate relative to the clamp main body, a state should be changed from the first state to the second state.

Accordingly, when a real blood collection is carried out after an initially flowing out blood is collected, the block-off member provided in the first tube becomes tearable after the second tube branched from the first tube of the blood collecting device is closed. That is, when the blood collecting device is operated, it is possible to surely prevent the block-off member from being torn and the first tube from being opened (communicated with) from the upstream side to the downstream side before the second tube is closed.

When the block-off member is torn off before the second tube is closed, even though the initially flowing out blood collecting operation completes, the initially flowing out flows in the blood collecting bag used for real blood collection. In this state, if the process transitions to real blood collection, the blood is contaminated by the initially flowing out blood already stored in the blood collecting bag, so that all collected blood must be disposed (the blood is wasted).

However, the present invention can surely prevent such a failure.

It is preferable that according to the clamp of the present invention, when the state is changed from the first state to the second state, the second tube should be closed before the tearing operation is enabled.

Accordingly, it becomes possible to further surely prevent the block-off member from being torn and the first tube from being opened from the upstream side to the downstream side before the second tube is closed.

It is preferable that according to the clamp of the present invention, the preventing portion should cover a part of the first tube where the block-off member is provided in the first state, and should be retracted from the covering part in the second state.

Accordingly, a tearing operation to the block-off member can be surely prevented.

It is preferable that according to the clamp of the present invention, the operation member should be a plate member, and the preventing portion should be a protrusion protrudingly formed from an outer circumference of the operation member toward an exterior.

Accordingly, a tearing operation to the block-off member can be surely prevented and cancelation of such a prevention are ensured.

It is preferable that according to the clamp of the present invention, the clamp main body should be a plate member and should be provided with a notch in an outer circumference thereof which is a cut-out of a portion corresponding to the block-off member, the operation member should be a plate member, and the preventing portion should include a portion of the outer circumference of the operation member facing the notch in the first state.

Accordingly, a tearing operation to the block-off member can be surely prevented and cancelation of such a prevention are ensured.

It is preferable that according to the clamp of the present invention, the pressing portion should include an inclined portion which is apart from the clamp main body and which gradually reduces a distance therefrom when the operation member is operated to rotate.

Accordingly, a rapid close of the second tube is suppressed, so that, for example, a back flow of the blood in the second tube can be prevented. Also, a rotational operation of the operation member becomes smooth.

It is preferable that according to the clamp of the present invention, the clamp main body should include a fixing portion that fixes the branched portion.

Accordingly, the first tube and the second tube are firmly fixed, so that it is possible to prevent the first tube and the second tube from being unintentionally displaced due to a rotational force when the operation member is operated to rotate.

It is preferable that according to the clamp of the present invention, the operation member should include an operation lever that is caught by a finger when the operation member is operated to rotate.

Accordingly, when the operation member is operated to rotate, the operation lever is pinched by fingers in order to rotate the operation member, so that the operability further improves.

It is preferable that the clamp of the present invention should further include restriction means for restricting a rotatable range of the operation member.

Accordingly, the clamp can be surely set in the first state and in the second state.

It is preferable that the clamp of the present invention should include a clamp main body and a preventing portion which is coupled to the clamp main body and which prevents a tearing operation to the block-off member, the clamp main body should include a pinching portion which presses and closes the second tube, and an operation portion for operating the pinching portion, and when the operation portion is operated, a state should be changed from the first state to the second state.

Accordingly, when a real blood collection is carried out after an initially flowing out blood is collected, the block-off member provided in the first tube becomes tearable after the second tube branched from the first tube in the blood collecting device is closed. That is, when the blood collecting device is operated, it is possible to surely prevent the block-off member from being torn and the first tube from being opened (communicated with) from the upstream side to the downstream side before the second tube is closed.

When the block-off member is torn before the second tube is closed, even though the initially flowing out blood collecting operation completes, the initially flowing out blood flows in the blood collecting bag used for real blood collection. In this state, if the process transitions to real blood collection, the blood is contaminated by the initially flowing out blood already stored in the blood collecting bag, so that all collected blood must be disposed (the blood is wasted).

However, the present invention can surely prevent such a failure.

It is preferable that according to the clamp of the present invention, in the first state, the preventing portion should cover a part of the first tube where the block-off member is provided and in the second state, the preventing portion should be retracted from the covering part.

Accordingly, a tearing operation to the block-off member can be surely prevented.

It is preferable that according to the clamp of the present invention, the preventing portion should be a long hollow member having a hollow opened in a direction opposite to a direction in which the preventing portion retracts.

Accordingly, a tearing operation to the block-off member can be surely prevented and cancelation of such a prevention are ensured.

It is preferable that according to the clamp of the present invention, the pinching portion should include: an abutting portion that abuts a part of an outer circumference of the second tube; and a pressing portion which is provided so as to face the abutting portion via the second tube, and which comes close to the abutting portion through the pressing operation, and presses the outer circumference of the second tube.

Accordingly, the middle portion of the second tube can be surely closed, and thus it is possible to prevent the blood from passing through the second tube and flowing downwardly in this state.

It is preferable that according to the clamp of the present invention, the preventing portion should include a long hollow member with a hollow, and the clamp main body and the hollow member should be arranged adjacent to each other and in parallel with each other.

Accordingly, the prevention for a tearing operation to the block-off member can be cancelled together with an operation of closing the second tube.

It is preferable that according to the clamp of the present invention, the hollow member should be coupled to the clamp main body in a rotatable manner relative to the clamp main body.

Accordingly, the first tube has not only a portion where the block-off member is provided but also other portions back and forth covered by the hollow member, so that a tearing operation to the block-off member is further surely prevented in the first state.

It is preferable that the clamp of the present invention should further include fixing means for fixing at least either one of the first tube and the second tube.

Accordingly, it is possible to surely prevent the clamp from being unintentionally displaced along the lengthwise direction of the tube, so that the operability when the clamp is operated improves.

In order to achieve the above object, the present invention provides a blood collecting device that includes: the clamp of the present invention; a first tube having one end and another end connected to a blood collecting needle and a blood bag, respectively; a second tube branched from a halfway of the first tube through a branched portion; and a block-off member which is provided in the first tube at the blood-bag side beyond the branched portion and which allows the first tube in a blocked state to be opened when torn, in which the clamp is arranged at the branched portion of the first tube.

Accordingly, it is possible to surely prevent the first tube from being opened before the second tube branched from the first tube in the blood collecting device is closed when the blood collecting device is operated.

BEST MODE FOR CARRYING OUT THE INVENTION

An explanation will be given of a clamp and a blood collecting device of the present invention through preferred embodiments shown in the accompanying drawings.

First Embodiment

Figure 1:
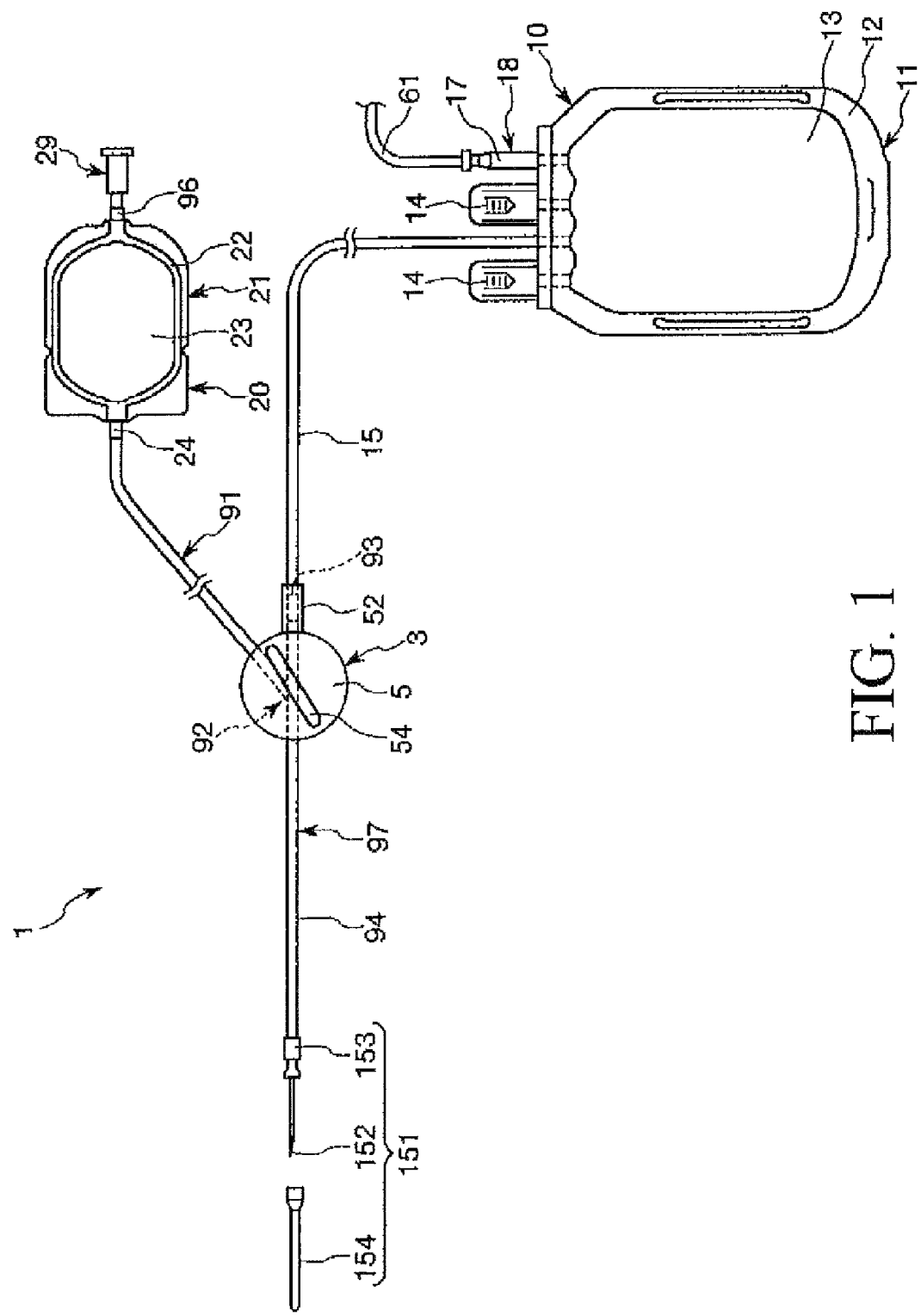
FIG. 1 is a schematic figure showing a blood collecting device according to a first embodiment of the present invention.
Figure 2:
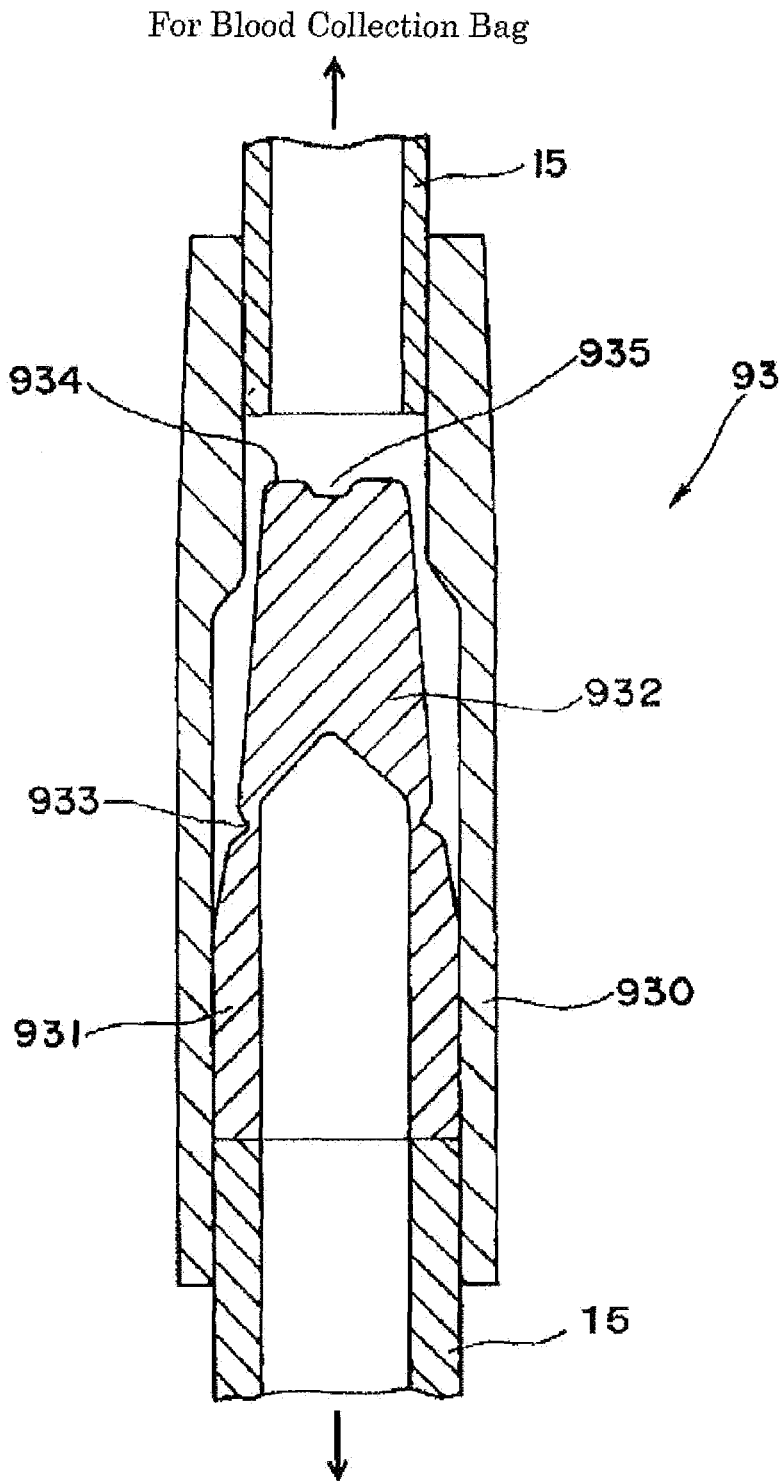
FIG. 2 is a vertical cross-sectional view showing an illustrative structure of a block-off member (tearable open member) of the blood collecting device shown in FIG. 1.
Figure 3:
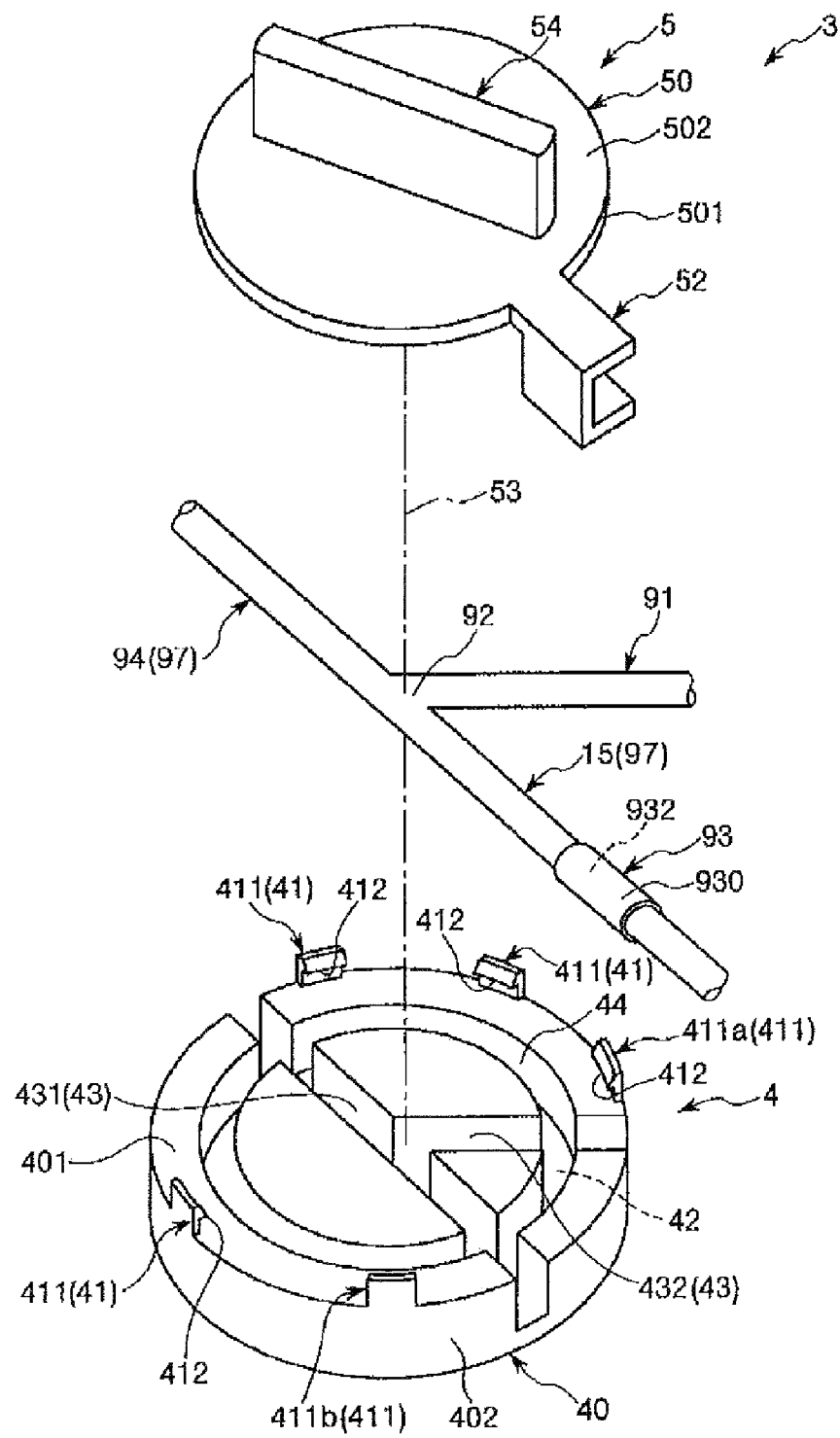
FIG. 3 is an exploded perspective view showing a clamp of the blood collecting device according to (the first embodiment of) the present invention.
Figure 4:
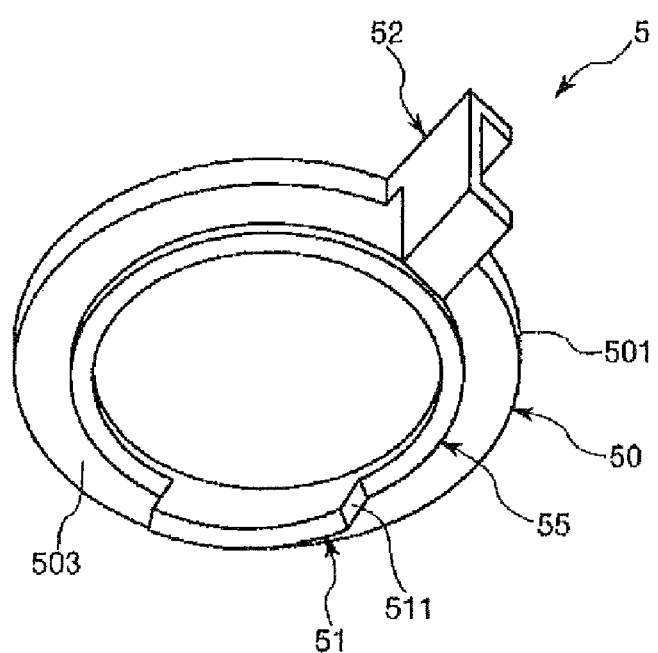
FIG. 4 is a perspective view showing an operation member (a second plate member) of the clamp shown in FIG. 3 as viewed from a bottom.
Figure 5:
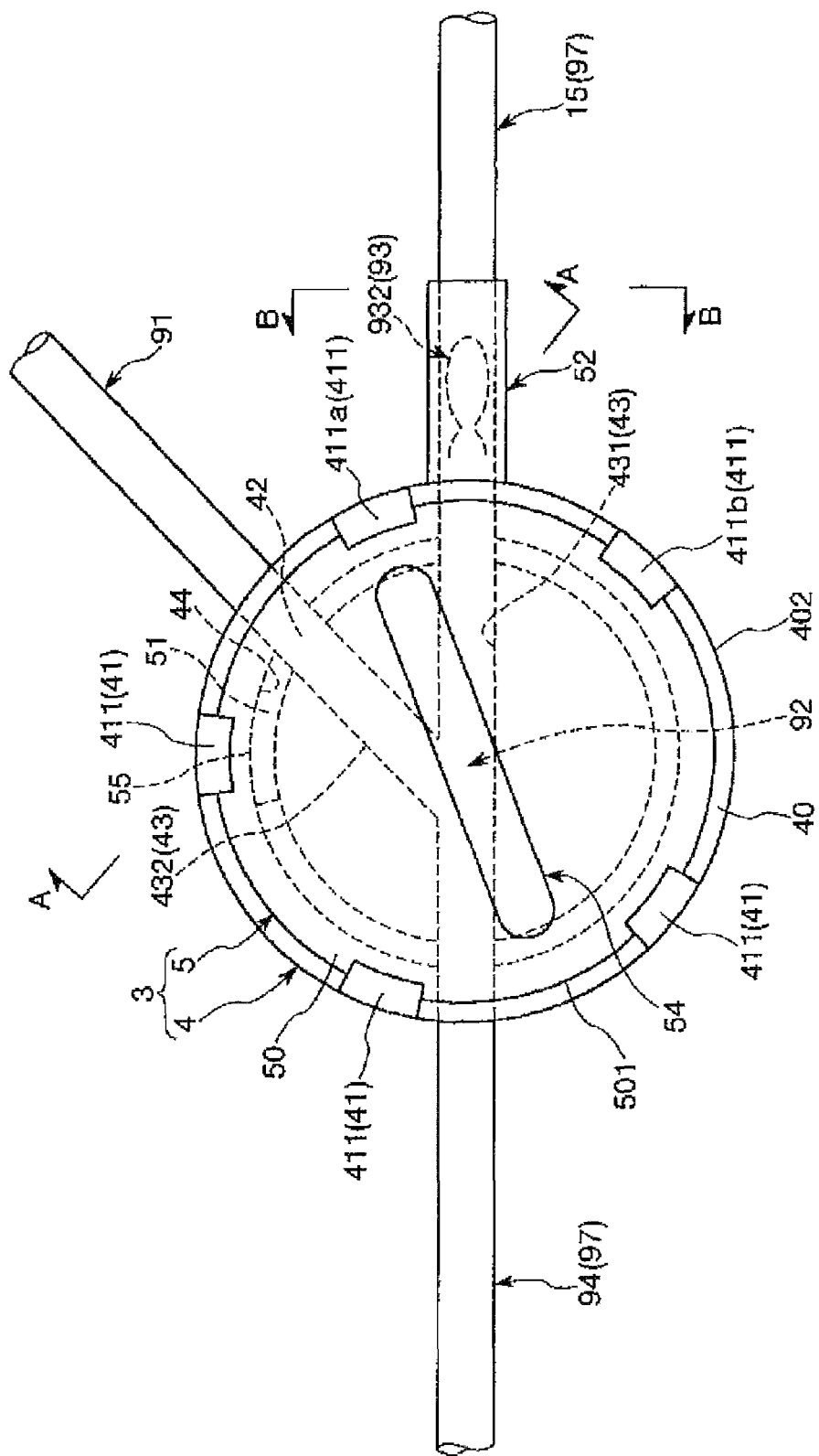
FIG. 5 is a plan view showing a first state of the clamp shown in FIG. 3.
Figure 6:
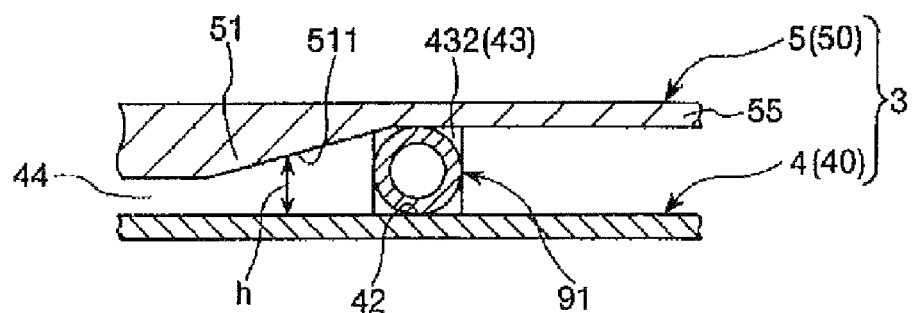
FIG. 6 is a cross-sectional view of the clamp cut along a line A-A in FIG. 5.
Figure 7:
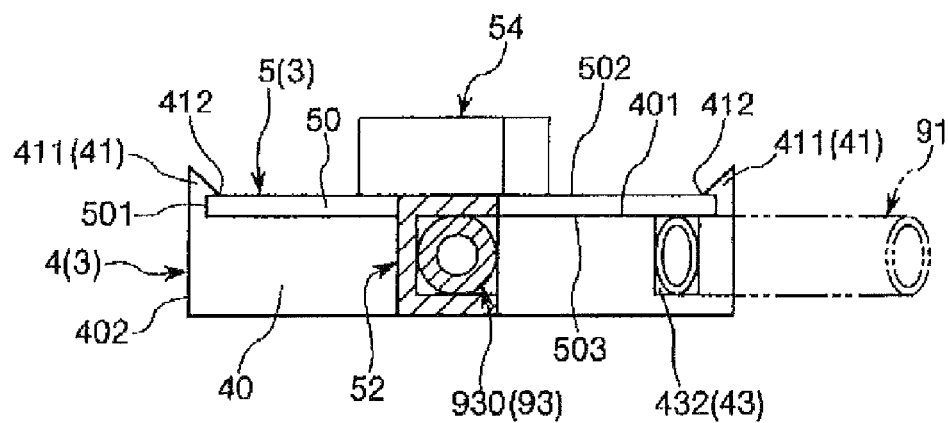
FIG. 7 is a cross-sectional view of the clamp cut along a line B-B in FIG. 5.
Figure 8:
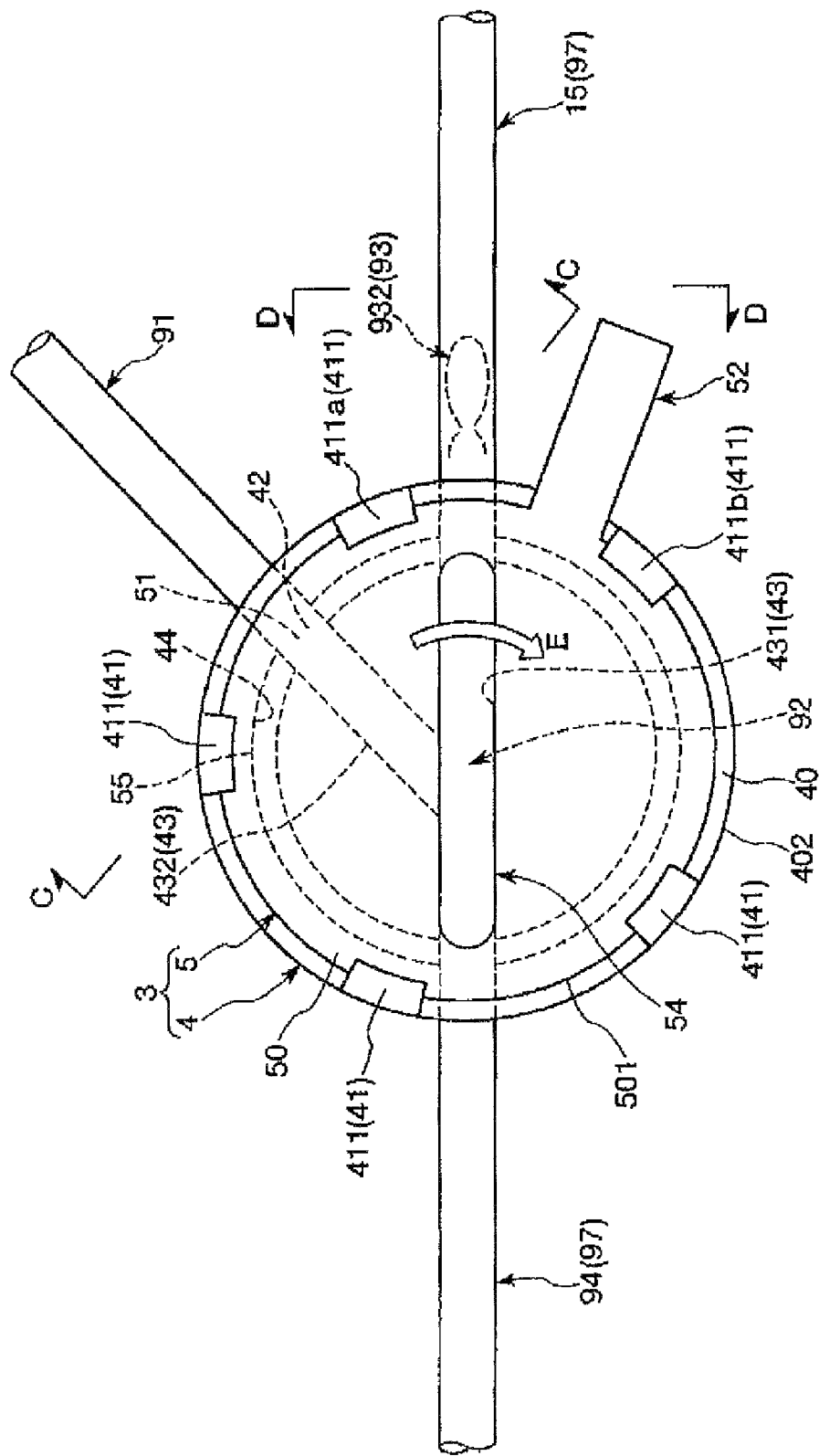
FIG. 8 is a plan view showing a second state of the clamp shown in FIG. 3.
Figure 9:
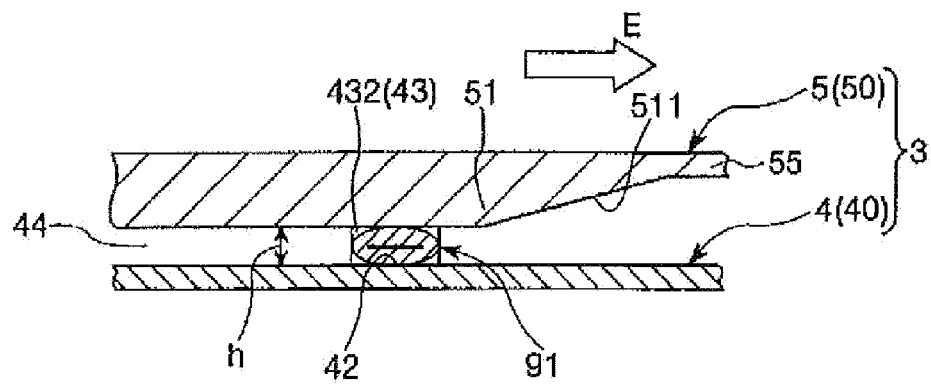
FIG. 9 is a cross-sectional view of the clamp cut along a line C-C in FIG. 8.
Figure 10:
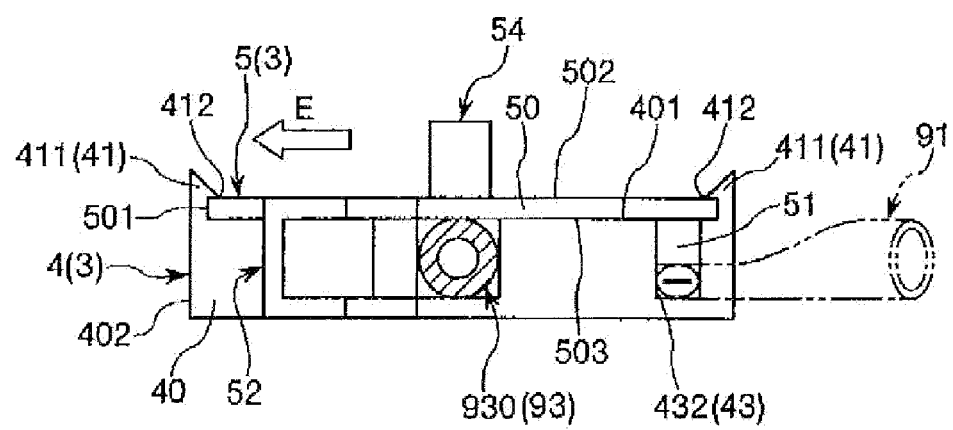
FIG. 10 is a cross-sectional view of the clamp cut along a line D-D in FIG. 8.

FIG. 1 is a schematic diagram showing a blood collecting device according to a first embodiment of the present invention. FIG. 2 is a vertical cross-sectional view showing an illustrative structure of a block-off member (tearable open member) of the blood collecting device shown in FIG. 1. FIG. 3 is an exploded perspective view showing a clamp of the blood collecting device according to (the first embodiment of) the present invention. FIG. 4 is a perspective view showing an operation member (a second plate member) of the clamp shown in FIG. 3 as viewed from a bottom. FIG. 5 is a plan view showing a first state of the clamp shown in FIG. 3. FIG. 6 is a cross-sectional view taken along a line A-A in FIG. 5. FIG. 7 is a cross-sectional view taken along a line B-B in FIG. 5. FIG. 8 is a plan view showing a second state of the clamp shown in FIG. 3. FIG. 9 is a cross-sectional view taken along a line C-C in FIG. 8, and FIG. 10 is a cross-sectional view taken along a line D-D in FIG. 8. In order to simplify the explanation, respective upper sides of FIGS. 3, 4, 6, 7, 9, and 10 (the same is true of FIGS. 13 and 14) are defined as "up" or "upward", and respective lower sides thereof are defined as "down" or "downward".

A blood collecting bag 1 shown in FIG. 1 includes a blood collecting needle 151, a blood collecting bag (a blood bag) 10 in which blood collected through the blood collecting needle 151 is stored, an initially flowing out blood bag (an inspection blood bag) 20 that collects (stores) initially flowing out blood collected through the blood collecting needle 151, i.e., blood initially flowing out of a body (inspection blood (collected initially flowing out blood)), and a plurality of tubes that function as lines interconnecting those with one another. Each component will be explained below.

The blood collecting bag 10 includes a main bag portion 11 which is in a pouched bag shape and formed of a couple of flexible material sheets made of a soft resin like polyvinyl chloride, which are adhered to each other at a sealed portion of their peripheral portion by fusing (e.g., thermal fusion, high frequency fusion) or bonding (joining).

A blood storage portion 13 that stores collected blood is formed inside a portion enclosed by the sealed portion 12 of the main bag portion 11. The blood collecting bag 10 is also used as a red-blood-cell bag that stores red blood cells, and in this case, the blood storing portion 13 stores and preserves concentrated red blood cells to which a red-blood-cell preservation solution is eventually added.

Two openings 14, 14, each of which can be sealed and opened by a peel tab, are formed on an upper portion of the main bag portion 11, and a discharging opening 18 is formed on a side of one of the opening 14. The discharging opening 18 is connected to one end of a tube 61 through a block-off member (a tearable open member) 17. One having the same structure as a block-off member 93 to be discussed later can be used as the block-off member 17.

It is not illustrated in the figure but another end of the tube 61 is connected to a white-blood-cell eliminating filter, a red-blood-cell bag (collecting bag), a blood plasma bag, and a bag filled with a red-blood-cell preservation solution through tubes. As a white-blood-cell eliminating filter, a filter of a type that eliminates blood platelets together with white blood cells is used. That is, the blood collecting device 1 configures a blood bag system.

Such a white-blood-cell eliminating filter of a type as collects exclusively white blood cells while allowing blood platelets to pass therethrough may be used, and in this case, a blood-platelet bag is further provided as well.

According to the present invention, the above-explained block-off member 17, discharging opening 18, and tube 61 may be omitted.

It is preferable that an anticoagulant should be put in the blood collecting bag 10 in advance. A liquid anticoagulant is ordinarily used, and may be, for example, an ACD-A solution, a CPD solution, a CPDA-1 solution, or a heparin-sodium solution. An amount of such anticoagulant is appropriately determined according to the amount of blood to be collected.

Furthermore, a flexible first tube (a blood collecting line (a blood collecting tube) 97 is connected to (coupled to) the upper portion of the main bag portion 11 so as to be communicated with the blood storing portion 13. The first tube 97 can be divided into a portion at an upstream side (the blood-collecting-needle-151 side) from a branched portion 92 where a second tube (a branched line (a branched tube)) 91 is branched and a portion at a downstream side (the blood-collecting-bag-10 side). Hereinafter, a portion of the first tube 97 at the upstream side from the branched portion 92, i.e., a portion connecting the branched portion 92 and the blood collecting needle 151 is referred to as a "tube 94". Moreover, a portion of the first tube 97 at the downstream side from the branched portion 92, i.e., a portion that connects the blood collecting bag 10 (the main bag portion 11) and the branched portion 92 is referred to as a "tube 15". Moreover, a clamp 3 to be discussed later is arranged at the branched portion 92.

The material of the first tube 97 and the second tube 91 is not limited to any particular one, and for example, the same material as that of the main bag portion 11 can be used.

The blood collecting needle 151 is attached to (connected to) an end (one end) of the tube 94 (the first tube 97) at the left of FIG. 1. The blood collecting needle 151 includes a needle body 152, a hub 153 that connects the needle body 152 and the tube 94 together, and a cap 154 that covers the needle body 152.

The second tube 91 is branched from the halfway of the first tube 97 through the branched portion 92. At the branched portion 92, the first tube 97 and the second tube 91 are branched in a "T" shape rotated counterclockwise by 90 degrees (see FIG. 1).

An initially flowing out blood bag 20 is connected to a right end of the second tube 91 in FIG. 1. The initially flowing out blood bag 20 includes a pouched main bag portion 21, a blood inlet (a blood flow-in portion) 24 which is provided at an upper end (one-end side) of the main bag portion 21 and which introduces an initially flowing out blood (blood) in the main bag portion 21, and a sampling port (a blood collecting port) 29 which is provided at a lower end (another-end side) of the main bag portion 21 and which collects the initially flowing out blood stored in the main bag portion 21.

The main bag portion 21 is formed by stacking flexible material sheets formed of a soft resin like polyvinyl chloride and by fusing (e.g., thermal fusion, high frequency fusion) or bonding (joining) a sealed portion 22 therearound.

A storage portion (an internal space) 23 is formed inside the portion enclosed by the sealed portion 22 of the main bag portion 21. The storage portion 23 (the interior of the main bag portion 21) retains (stores) initially flowing out blood that has passed through the blood collecting needle 151 (the needle body 152), the tube 94, the branched portion 92, and the second tube 91 successively in this order.

The tubular blood inlet 24 is provided at the center of the upper end (one-end side) of the main bag portion 21. The blood inlet 24 is communicated with the storage portion 23, and the second tube 91 and the storage portion 23 are communicated with each other through the blood inlet 24.

The blood inlet 24 may be formed integrally with the main bag portion 21, or a tubular member that is a separate piece from the main bag portion 21 may be coupled to the main bag portion 21. Also, the length of the blood inlet 24 is not limited to any particular size, and may be longer or shorter than that of the illustrated example.

A tubular blood outlet 96 is provided at the lower end (another-end side) of the main bag portion 21. The blood outlet 96 is communicated with the storage portion 23, and the sampling port 29 and the storage portion 23 are communicated with each other through the blood outlet 96.

The blood outlet 96 may be integrally formed with the main bag portion 21, or a tubular member that is a separate piece from the main bag portion 21 may be coupled to the main bag portion 21. Also, the length of the blood outlet 96 is not limited to any particular size, and may be longer or shorter than the illustrated example, but the shorter length is preferable since a risk of aeration can be reduced when the initially flowing out blood in the main bag portion 21 is collected from through the sampling port 29.

The sampling port 29 is cylindrical, and has a pressure-reduction blood collecting tube (unillustrated) in the interior thereof connected in a freely detachable manner. The initially flowing out blood in the main bag portion 21 is collected into the pressure-reduction blood collecting tube connected to the sampling port 29.

The tube 15 is provided with the block-off member (a tearable open member) 93 in the vicinity of the branched portion 92.

As shown in FIG. 2, the block-off member 93 includes a short tube 930 formed of a flexible resin like soft polyvinyl chloride, and a cylindrical portion 931 which is so tightly fitted in the short tube 930 that no water passes through between them and which has one end closed by a solid column portion 932.

An end portion of the tube 15, with which the block-off member 93 is connected, is cut, and the cut portion is complemented with the short tube 930. Therefore, the short tube 930 can be deemed as a component of the tube 15.

A thin and brittle tearable portion 933 is formed around the outer circumference of the cylindrical portion 931. When the short tube 930 is bent by applying an external force on the outer surface of the short tube 930 with a finger, etc., the solid column portion 932 is bent and separated with the tearable portion 933 torn. As a result, the inner passage of the tube 15 (the first tube 97), which is blocked off (discontinued) by the solid column portion 932 and corresponds to an upstream portion of the tube 15 (the blood-collecting-needle-151 side) becomes in communication with an downstream portion of the tube 15 (the initially flowing out blood bag-20 side).

The material of the cylindrical portion 931 is not limited to any particular one, and examples of such are hard materials, such as hard polyvinyl chloride, polycarbonate, and polyester.

The upper portion of the solid column 932 in FIG. 2 is in a wedge shape, and it is preferable that the upper end thereof (a tip) 934 should have a smaller dimension in the width direction than the outer diameter of the cylindrical portion 931 and a larger dimension than the inner diameter of the tube 15 so that the solid column 932 does not block off the tube 15 after the solid column 932 is torn off and separated. Also, as is shown in the figure, the upper end 934 of the solid column 932 may be provided with a groove 935 that promotes the mobilization of blood.

As explained above, the clamp 3 is disposed at the branched portion 92 (see FIG. 1).

As shown in FIG. 3, the clamp 3 includes a pair of plate members, i.e., a first plate member (a clamp main body) 4 and a second plate member (an operation member) 5. The clamp 3 has the first plate member 4 and the second plate member 5 superimposed (facing) with each other, and the second plate member 5 can be rotated relative to the first plate member 4 around an axis (rotation center 53) vertical to the plane direction. The clamp 3 can change a state between a first state (an initial state) shown in FIG. 5 and a second state shown in FIG. 8 by this rotational operation (in accordance with a rotation angle of the second plate member 5 relative to the first plate member 4). Each component will be explained below.

The material of the first plate member 4 and the second plate member 5 is not limited to any particular one, and examples of such a material are various kinds of resin, such as polyvinyl chloride, polyethylene, polypropylene, cyclic polyolefin, polystyrene, poly-(4-methylpentene-1), polycarbonate, an acrylic resin, an acrylonitryle-butadiene-styrene copolymer, polyester like polyethylene-terephthalate and polyethylene-naphthalate, butadiene-styrene copolymer, and polyamide (e.g., nylon 6, nylon 6.6, nylon 6.10, and nylon 12). Among those, from the standpoint of easiness of molding, resins, such as polypropylene, cyclic polyolefin, and polyester are preferable. Moreover, it is preferable that the material of the first plate member 4 and the second plate member 5 should be substantially transparent in order to ensure the visibility of the interior of the clamp 3, i.e., the vicinity of the branched portion 92.

As shown in FIG. 3, the first plate member 4 includes a main body 40 in a discoidal shape, support portions (guides) 41 that rotatably support the second plate member 5, a first press closing portion (a press closing portion) 42 that presses the second tube 91 against the second plate member 5 (a second press closing portion 51) and closes the second tube 91, and a fixing portion 43 that fixes the branched portion 92 and its vicinity tubes.

The support portion 41 include a plurality of (in this embodiment, five) protrusions 411 formed protrudingly to the upward direction on a top face 401 of the main body 40. Those protrusions 411 are arranged along the circumferential direction of the main body 40 (the first plate member 4) at an equal interval. The second plate member 5 is disposed inside these protrusions 411, and has an outer periphery portion 501 in connection with and held by respective protrusions 411. Accordingly, the position of the second plate member 5 in the radial direction is regulated (see FIGS. 7 and 10).

Each protrusion 411 is provided with a claw 412 protruding inwardly. The edge of an upper face 502 of the second plate member 5 is engaged with each claw 412 of each protrusion 411. Accordingly, the position of the second plate member 5 in the vertical direction is restricted (see FIGS. 7 and 10).

The second plate member 5 is thus rotatably supported by the support portions 41.

The claw 412 of each protrusion 411 can receive a counterforce from the second tube 91 acting on the second plate member 5 when the second tube 91 is closed by being pressed.

The fixing portion 43 includes a first groove 431 and a second groove 432 formed in the top face 401 of the main body 40 (see FIG. 3).

The first groove 431 is a linear groove passing through the center of the main body 40, and is opened to the outer circumference (the side face) 402 of the main body 40. A part of the first tube 97 (the vicinity of the branched portion 92) is inserted in the first groove 431 (see FIGS. 5 and 8).

The second groove 432 is a linear groove branched from the center of the first groove 431. Like the first groove 431, the second groove 432 is also opened to the outer circumference (the side face) 402 of the main body 40. A part of the second tube 91 (a part in the vicinity of the branched portion 92 side) is inserted in the second groove 432.

Such a fixing portion 43 fixes the first tube 97 and the second tube 91 without fail. Accordingly, unwanted misalignment (a rotation together with the second plate member 5) of the first tube 97 with the second tube 91 that could occur when the second plate member 5 is operated to rotate can be prevented without fail.

As shown in FIG. 3, a third groove 44 in an annular shape formed coaxially about the center of the main body 40 is formed in the top face 401 thereof. The third groove 44 intersects with the first groove 431 at two locations, and intersects with the second groove 432 at one location. The portion of the third groove 44 intersecting with the second groove 432, that is, a portion where the second tube 91 traverses, has a bottom that serves as the first press closing portion 42 (see FIGS. 5, 6, 8 and 9).

As shown in FIG. 3, the second plate member 5 is disposed above the first plate member 4 through the branched portion 92 so as to have the first plate member 4 and the second plate member 5 coaxially disposed. As explained above, the second plate member 5 is rotatable, and the rotation center 53 thereof is on the branched portion 92 in a planar view (see FIG. 3). According to such an arrangement, the operation for rotating the second plate member 5 is facilitated. As a result the clamp 3 can be more easily operated.

The second plate member 5 includes a main body 50 in a discoidal shape, a second press closing portion (pressing portion) 51 that is capable of pressing and closing the second tube 91 on the first plate member 4 (the first press closing portion 42), a preventing portion 52 that prevents a tearing operation performed on the block-off member 93, and an operation lever 54 caught by fingers when the second plate member 5 is operated to rotate.

As shown in FIG. 4, an annular rib 55 coaxial about the center of the main body 50 is protrudingly formed on a bottom face 503 of the main body 50 (the second plate member 5). The rib 55 is inserted in the third groove 44 of the first plate member 4.

The rib 55 is provided with a portion higher than the other portion, and this portion functions as the second press closing portion 51.

As shown in FIGS. 6 and 9, in the clamp 3, the first press closing portion 42 of the first plate member 4 and the second press closing portion 51 of the second plate member 5 are apart from each other. As the second plate member 5 rotates, a distance h between the first press closing portion 42 and the second press closing portion 51 changes. As a result, the second press closing portion 51 comes closer to or farther from the first press closing portion 42.

As shown in FIG. 6, when the clamp 3 is in the first state, the distance h between the first press closing portion 42 and the second press closing portion 51 is the largest. That is, the second press closing portion 51 is most apart from the first press closing portion 42. In this state, the second tube 91 is not pressed nor closed by the first press closing portion 42 and the second press closing portion 51. Accordingly, the upper stream portion of the second tube 91 is in communication with the downstream portion of the second tube 91 and an initially flowing out blood passing through the tube 94 can flow into the initially flowing out blood bag 20 through the second tube 91. At this time, since the block-off portion 93 is not torn yet, the initially flowing out blood flowing through the tube 94 is prevented from flowing into the blood collecting bag 10 passing further through the tube 15 (see FIG. 5).

Next, when the second plate member 5 is operated to rotate from the first state, the clamp 3 becomes in a second state as shown in FIG. 9.

In the second state, the distance h between the first press closing portion 42 and the second press closing portion 51 becomes the smallest. That is, the second press closing portion 51 comes closest to the first press closing portion 42. Accordingly, the second tube 91 is pressed and closed between the first press closing portion 42 and the second press closing portion 51 without fail. In this state, blood flowing through the tube 94 is prevented from flowing into the initially flowing out blood bag 20 through the second tube 91.

The second press closing portion 51 has an inclined portion 511 (see FIG. 9) at an end portion which comes ahead of the other portion in the rotation direction (a direction indicated by an arrow E) of the second press closing portion 51 when the second plate member 5 is rotated. Over the inclined portion 511, the distance h gradually changes (decreases) along the rotation direction of the second plate member 5. Accordingly, the second tube 91 is prevented from being rapidly pressed and closed, and thus a backflow of the initially flowing out blood in the second tube 91 for example is suppressed. Also, the rotation operation is performed smoothly.

The second press closing portion 51 provided with such an inclined portion 511 functions as a pressing portion which presses the second tube 91 on the first plate member 4 and closes the second tube 91.

As shown in FIGS. 3 and 4, the preventing portion 52 is provided at the outer circumference 501 of the main body 50 in the form of a protrusion protruding toward the radial direction (the outward direction). The preventing portion 52 prevents a tearing operation given to the block-off member 93 in the first state (see FIGS. 5 and 7).

As shown in FIG. 7, the preventing portion 52 is in such a shape as enclosing the block-off member 93 (the short tube 930), that is, a rectangular cross-sectional shape opened on its rear side when the preventing portion 52 is retracted in a direction (a direction indicated by the arrow E). Accordingly, when the clamp 3 is in the first state, the block-off member 93 is covered by the preventing portion 52, so that the block-off member 93 cannot be held by a finger, etc., and a tearing operation given to the block-off member 93 can be prevented without fail.

As shown in FIG. 8, when the clamp 3 is in the second state, the preventing portion 52 retracts from the block-off member 93 along with the rotation of the second plate member 5. Accordingly, a state in which a tearing operation is prevented by the preventing portion 52 is cancelled, i.e., the block-off member 93 is exposed, and a tearing operation by holding block-off member 93 is enabled.

The preventing portion 52 can move between two protrusions 411a and 411b adjoining to each other shown in FIG. 5 (and FIGS. 3 and 8) among the five protrusions 411 of the first plate member 4. Accordingly, the rotatable range of the second plate member 5 is restricted. Accordingly, the clamp 3 can be surely set to be in the first state in which the second tube 91 is opened and a tearing operation to the block-off member 93 is prevented and in the second state in which the second tube 91 is closed and a tearing operation to the block-off member 93 is enabled.

According to the clamp 3, the protrusions 411a and 411b can be deemed as restriction means for restricting the rotatable range of the second plate member 5.

As shown in FIG. 3, an operation lever 54 is protrudingly formed on the top face 502 of the main body 50 (the second plate member 5). The operation lever 54 is a plate member provided on the main body 50 in a standing manner. Moreover, as shown in FIG. 8, the operation lever 54 is disposed in the same direction as the running direction of the first tube 97 when the clamp 3 is in the second state.

A rotation operation can be performed by the operation lever 54 formed in this fashion while the operation lever 54 is caught by fingers when the second plate member 5 is operated to rotate. Accordingly, the operation is further facilitated.

Next, an explanation will be given of the working of the blood collecting device 1 (an operated state (a use state) of the clamp 3).

As shown in FIG. 1, firstly the blood collecting device 1 has the clamp 3 in the first state. Accordingly, the tube 94 of the first tube 97 and the second tube 91 are communicated with each other (see FIGS. 5 and 6). Moreover, the tube 15 of the first tube 97 is in a closed (blocked) state by the block-off member 93. According to such a blood collecting device 1, when the blood collecting needle 151 is stuck on a donor, blood from the tube 94 flows in the second tube 91 through the branched portion 92.

Moreover, as explained above, since the block-off member 93 is covered by the preventing portion 52 of the second plate member 5, a tearing operation is disabled (see FIGS. 5 and 7).

Furthermore, the blood collecting bag 10 and the initially flowing out blood bag 20 of the blood collecting device 1 are respectively set at a location lower than a portion where the blood collecting needle 151 is stuck.

Next, the cap 154 is removed from the blood collecting needle 151 (see FIG. 1), the blood collecting needle 151 is stuck into a vein (a blood vessel) of the donor, and when it is confirmed that the blood collecting needle 151 is stuck in a vein, the hub 153 is fixed with, for example, an adhesive tape to the vicinity of the location where the blood collecting needle is stuck on a donor. Likewise, it is preferable that the first tube 97 (the tube 94) should be fixed to the vicinity of the location where the blood collecting needle is stuck by means of an adhesive tape.

Through such operations, an initially flowing out blood (blood) flows in the second tube 91 through the blood collecting needle 151, the tube 94, and the branched portion 92, flows through the second tube 91, and is introduced in the storage portion 23 of the initially flowing out blood bag 20. In this case, since the flow path of the tube 15 is blocked by the block-off member 93, the blood flows in the second tube 91 from the tube 94 through the branched portion 92 without fail.

Before the blood is introduced, air in the tube 94 and the second tube 91 is discharged from those tubes, and is collected in the initially flowing out blood bag 20. Accordingly, the pressures inside the tube 94 and the second tube 91 and the volumes of the inner cavity of the tube 94 and that of the second tube 91 are maintained at substantially constant. As a result, application of an excessive load on blood cells can be suppressed, and thus it becomes possible to suppress production of hemolysis or the like in the blood. Moreover, no blood enters the block-off-member-93 at the branched portion 92 and is left there.

When the liquid level of the initially flowing out blood in the storage portion 23 of the initially flowing out blood bag 20 reaches a target position in the initially flowing out blood bag 20, the operation lever 54 of the second plate member 5 of the clamp 3 is operated in order to set the clamp 3 to be in the second state. Accordingly, the flow path of the second tube 91 becomes in a closed state (see FIGS. 8 and 9).

Thus the blood collecting device 1 collects (obtains) a predetermined amount (a target amount) of blood in the initially flowing out blood bag 20. Through the initially flowing out blood collecting operation, an initially flowing out blood that may be contaminated by bacteria in some cases can be collected (removed) from the blood to be collected from the donor. Accordingly the bacteria is prevented from mixing in the blood collected in the blood collecting bag 10 to be discussed later, thereby improving the safeness of a blood product.

Moreover, as explained above, in the second state, the preventing portion 52 of the second plate member 5 is retracted from the block-off member 93, and the block-off member 93 is exposed, so that a tearing operation to the block-off member 93 is enabled (see FIGS. 8 and 10).

Furthermore, it is preferable that the second tube 91 should be pressed and closed before a tearing operation on the block-off member 93 is enabled when the clamp 3 becomes in the second state from the first state. That is, when the clamp 3 is in a transition from the first state to the second state, it is preferable that the second tube 91 should be completely pressed and closed but the block-off member 93 should not be completely exposed (about to be completely exposed). Such a condition can be realized by setting, for example, a positional relationship between the second press closing portion 51 of the second plate member 5 and the preventing portion 52 thereof appropriately.

Next, blood collection (real blood collection operation) into the blood collecting bag is started.

In this case, the tearable portion 933 of the exposed block-off member 93 is torn in order to separate the solid column 932, thereby opening the flow path in the block-off member 93. Through this operation, the flow path of the first tube 97 is kept opened with the upstream side portion in communication with the downstream side portion. Accordingly, the collected blood flows through the first tube 97, and is introduced in the blood storing portion 13 of the blood collecting bag 10. Therefore, the blood collecting bag 10 storing the blood excluding the initially flowing out blood is removed (collected) is obtained.

While the blood is being collected into the blood collecting bag 10, the pressure-reduction blood collecting tube is inserted in the sampling port 29 of the initially flowing out blood bag 20 and the blood stored in the initially flowing out blood bag 20 is collected (sampling) in the pressure-reduction blood collecting tube. Thereafter, the pressure-reduction blood collecting tube which has collected the blood is removed from the sampling port 29. When the blood is sampled into a plurality of pressure-reduction blood collecting tubes, this operation is repeated.

Such sampling may be performed after the blood collection into the blood collecting bag 10 completes.

In the blood collection into the blood collecting bag 10, after a predetermined amount of blood is collected in the blood collecting bag 10, the blood collecting needle 151 is taken out from the blood vessel of the donor, and the first tube 97 and the second tube 91 are closed by fusing using a tube sealer if need be. Thereafter, the initially flowing out blood bag 20 and the blood collecting needle 151 are taken out.

Moreover, the blood stored (collected) in the blood collecting bag 10 is made to pass through a white-blood-cell removing filter in order to separate white blood cells and blood platelets, the remaining blood components are collected in a collecting bag, and the blood collecting bag 10 and the white-blood-cell removing filter are taken out. Thereafter, the blood in the collecting bag undergoes a centrifugal separation, is separated into red-blood-cell layers and blood plasma layers, and after the blood plasma is transferred into a blood plasma bag, a red-blood-cell preservation liquid in the bag filled with the red-blood-cell preservation liquid is added to the concentrated red blood cells left in the collecting bag, and is mixed therewith.

On the other hand, the initially flowing out blood collected in the pressure-reduction blood collecting tube is used for examinations, such as a biochemical examination of blood serum, and a nucleic acid amplification examination of infective viruses (e.g., AIDS virus, and hepatitis virus).

As explained above, according to the blood collecting device 1 (the clamp 3), when the real blood collection is carried out after the initially flowing out blood is collected, the block-off member 93 provided in the first tube 97 becomes tearable after the second tube 91 is closed. That is, when the blood collecting device 1 is operated, it is possible to prevent without fail the block-off member 93 provided in the first tube 97 from being torn and the first tube 97 from being opened (communicated) with the upstream side portion in communication with the downstream side portion before the second tube 91 is closed.

If the block-off member 93 is torn before the second tube 91 is closed, the initially flowing out blood flows into the blood collecting bag 10 used for real blood collection even though the initially flowing out blood collecting operation is completed. Then if the real blood collection gets started after this operation, the blood is contaminated by the initially flowing out blood already stored in the blood collecting bag 10 and all collected blood must be disposed (the collected blood is wasted).

According to the blood collecting device 1 (the clamp 3), however, such a failure can be surely prevented.

Second Embodiment

Figure 11:
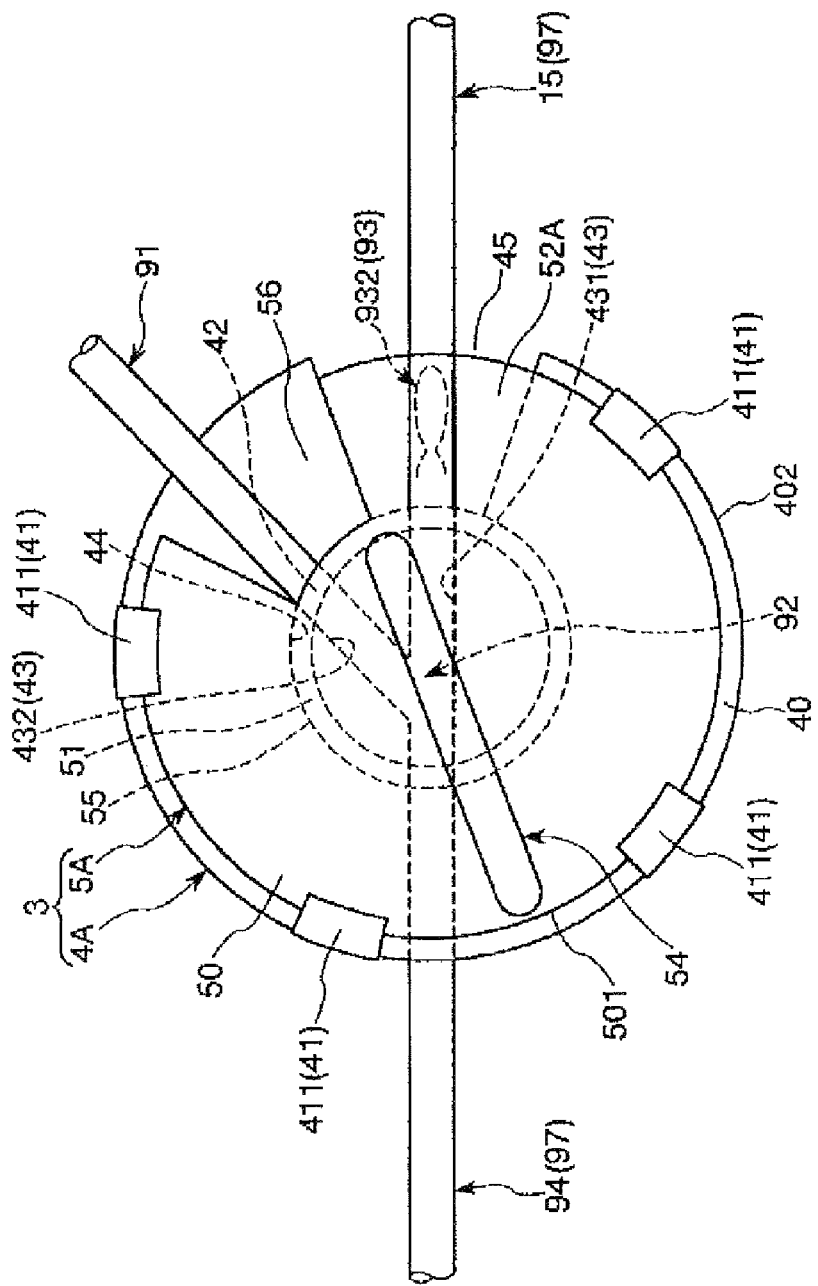
FIG. 11 is a plan view showing a first state of a clamp according to (a second embodiment of) the present invention.
Figure 12:
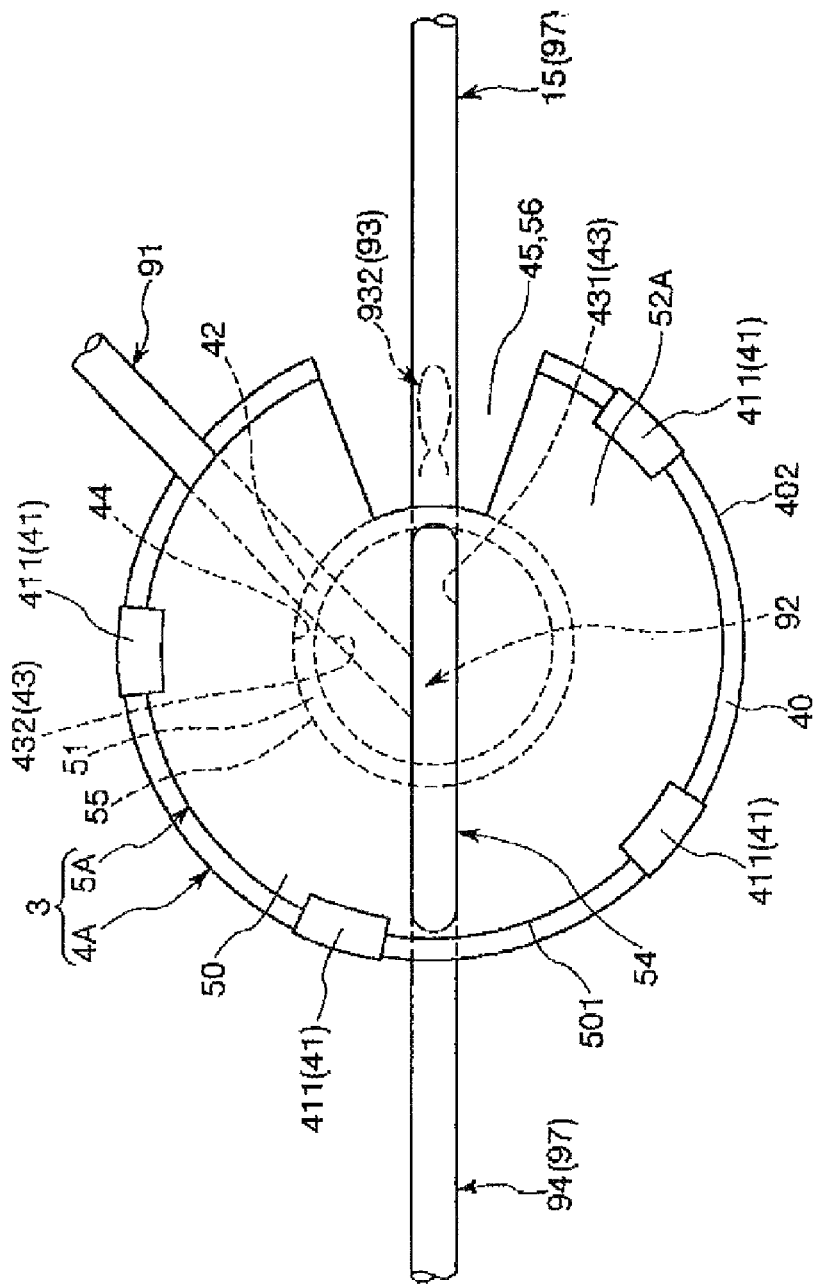
FIG. 12 is a plan view showing a second state of the clamp according to (the second embodiment of) the present invention.

FIG. 11 is a plan view showing a first state of a clamp according to (a second embodiment of) the present invention, and FIG. 12 is a plan view showing a second state of the clamp according to (the second embodiment of) the present invention.

An explanation will be given of the clamp and a blood collecting device according to the second embodiment of the present invention with reference to those figures, but the difference from the foregoing embodiment will be mainly explained and the explanation for the same matter will be omitted.

This embodiment is the same as the first embodiment except the structure (the shape) of the preventing portion that is different.

As shown in FIGS. 11 and 12, a notched portion 45 is formed on the outer circumference 402 of a first plate member 4A (the main body 40). The notched portion 45 is a cut-out of the outer circumference 402 facing (corresponding to) the block-off member 93. The notched portion 45 is in a sectorial shape.

As shown in FIG. 11, when the clamp 3 is in the first state, a portion of the outer circumference of a second plate member 5A is disposed opposite (faces) the notched portion 45 of the first plate member 4A through the block-off member 93. The portion of the second plate member 5A facing the notched portion 45 is an preventing portion 52A. This preventing portion 52A covers the block-off member 93 in the first state, and thus a tearing operation to the block-off member 93 can be prevented without fail.

As shown in FIG. 12, a notched portion 56 is formed at such a position on the outer circumference of the second plate member 5A that the notched portion 56 is aligned with (overlapping) the notched portion 45 of the first plate member 4A when the clamp 3 is in the second state. Like the notched portion 45, the notch 56 is in a sectorial shape. According to such a structure, in the second state, the block-off member 93 is exposed through the notches 45 and 56, so that the block-off member 93 becomes holdable and thus a tearing operation thereof is surely enabled.

Third Embodiment

Figure 13:
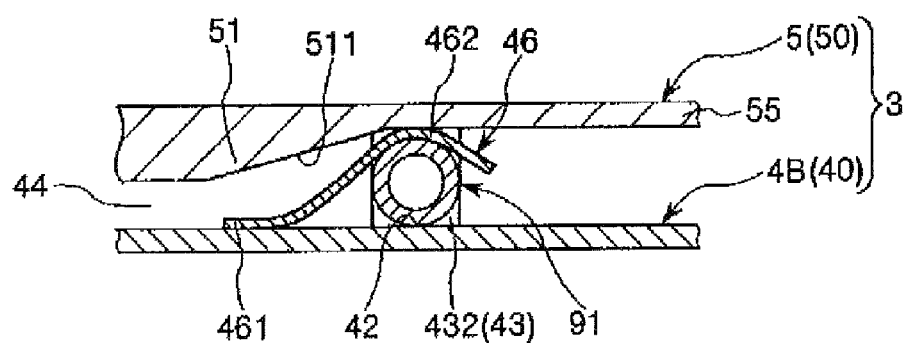
FIG. 13 is a vertical cross-sectional view showing a first state of a clamp according to (a third embodiment of) the present invention.
Figure 14:
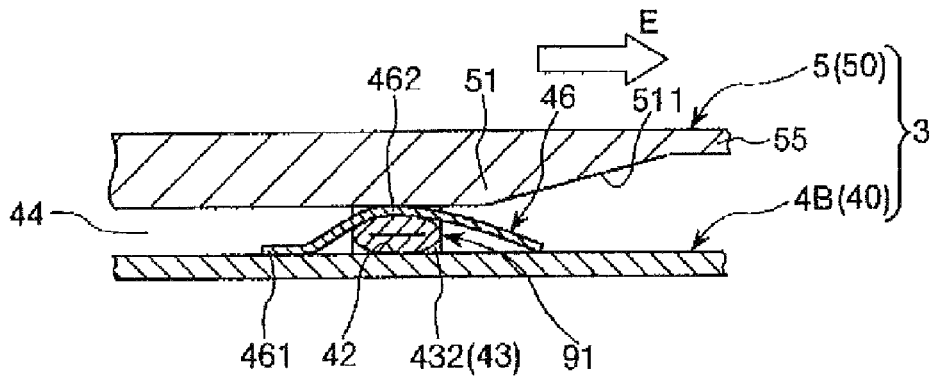
FIG. 14 is a vertical cross-sectional view showing a second state of the clamp according to (the third embodiment of) the present invention.

FIG. 13 is a vertical cross-sectional view showing a first state of a clamp according to (a third embodiment of) the present invention, and FIG. 14 is a vertical cross-sectional view showing a second state of the clamp according to (the third embodiment of) the present invention.

An explanation will be given of the clamp and a blood collecting device according to the third embodiment of the present invention with reference to those figures, but the difference from the foregoing embodiment will be mainly explained and the explanation for the same matter will be omitted.

This embodiment is same as the first embodiment except that a clamp has a protecting sheet.

As shown in FIGS. 13 and 14, a first plate member 4B (the main body 40) has a flexible protecting sheet 46 provided on the bottom (the first press closing portion 42) of the third groove 44. The protecting sheet 46 has a function to reduce a frictional resistance with the second plate member 5 during the rotation operation.

The protecting sheet 46 has one end portion (the left in FIG. 13 (and FIG. 14)) which is a fixed portion 461 fixed to the bottom of the third groove 44 by means of, for example, an adhesive, and has another end portion which is opposite to the fixed portion 461 of the protecting sheet 46 and which is a covering portion 462 covering the second tube 91.

The material of the protecting sheet 46 is not limited to any particular one, and for example, polytetrafluoroethylene (PTFE) can be used.

Since the protecting sheet 46 covers the second tube 91, when the second plate member 5 is rotated, it is possible to prevent the rotation force from acting on the second tube 91, so that a twisting of the second tube 91 can be prevented without fail.

Note that instead of providing the protecting sheet 46, a surface treatment may be performed on the second press closing portion 51 of the second plate member 5 or the second tube 91 in order to reduce a frictional resistance.

Fourth Embodiment

Figure 15:
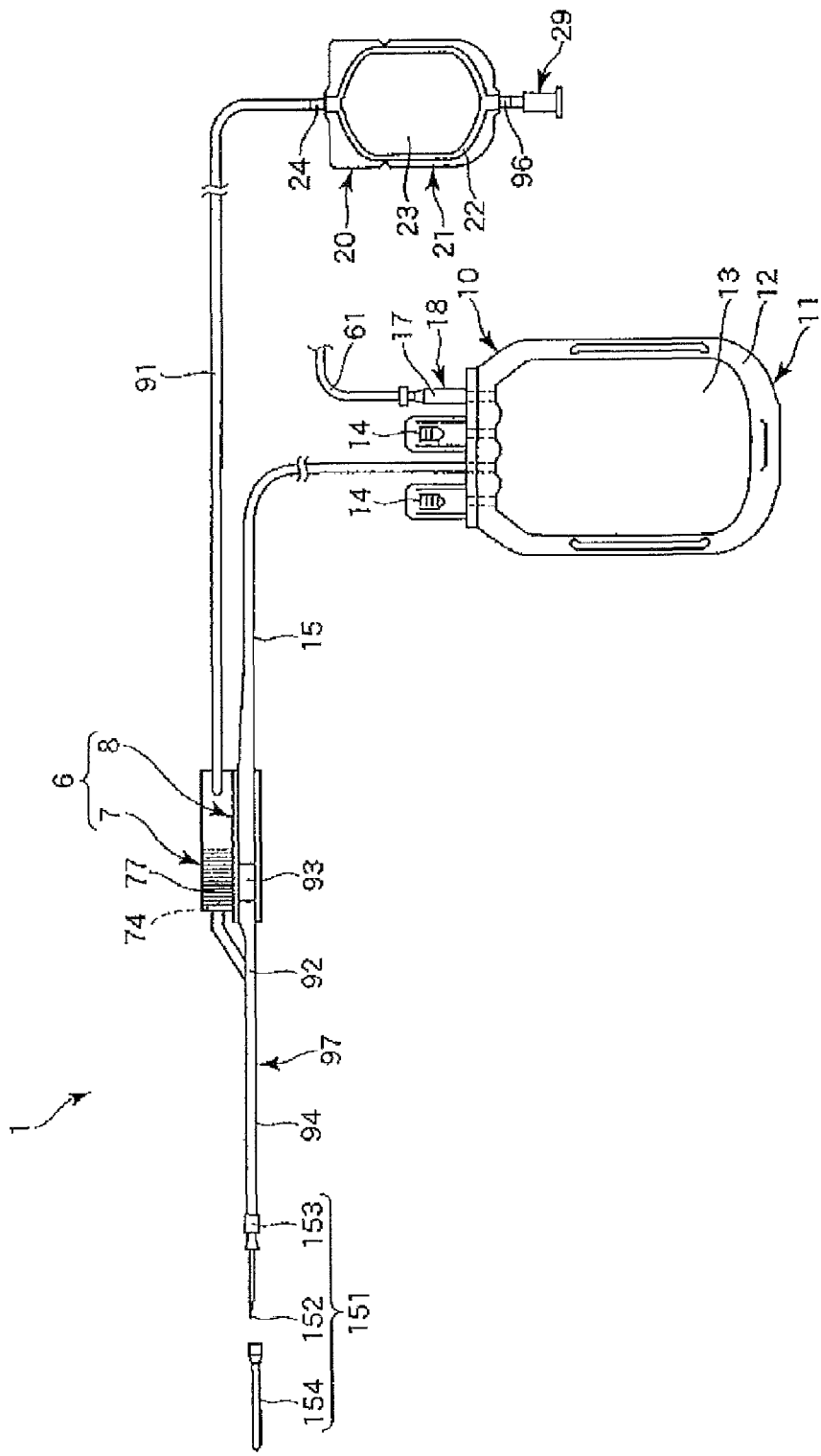
FIG. 15 is a schematic view (a plan view) showing a blood collecting device according to a fourth embodiment of the present invention.
Figure 16:
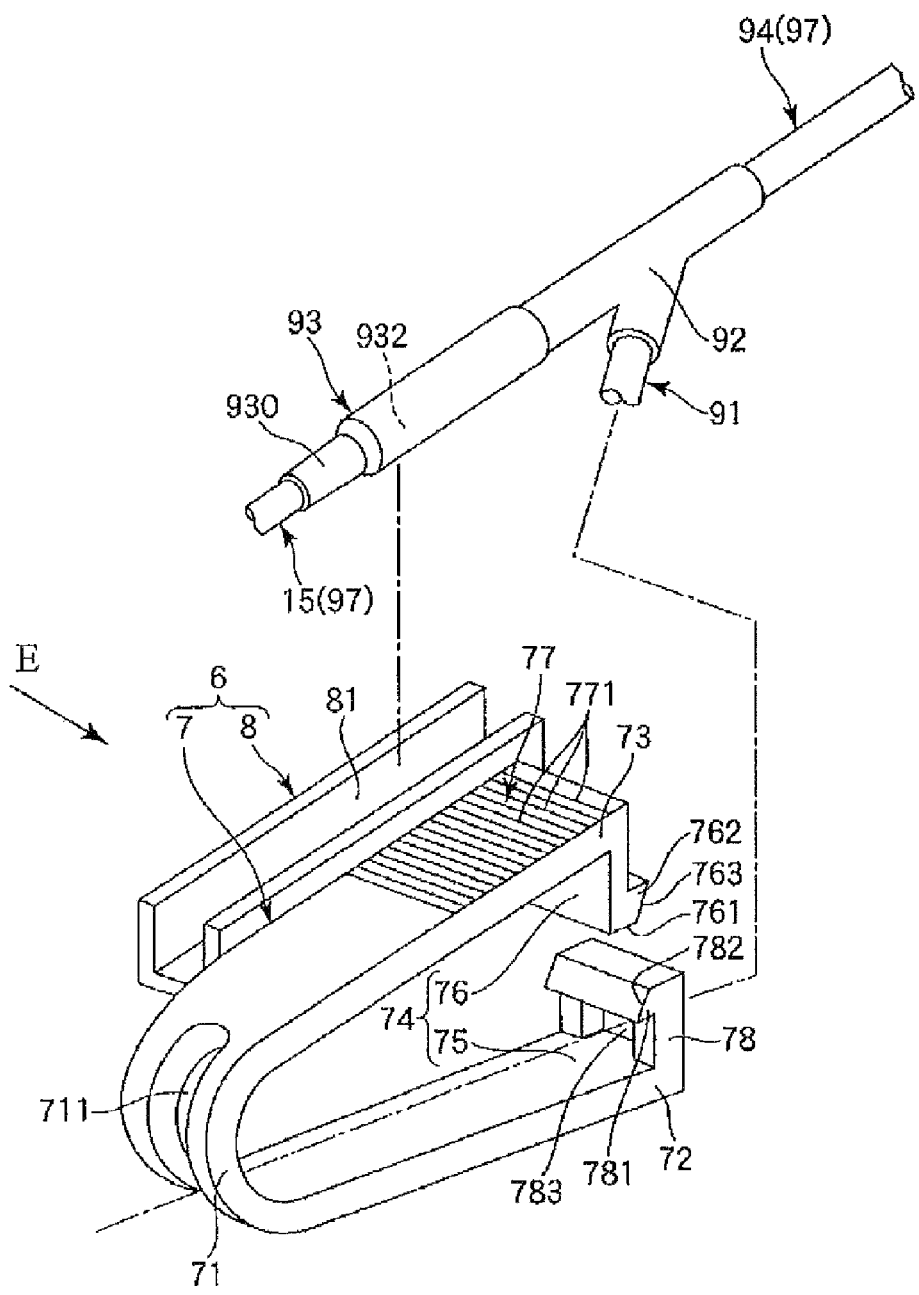
FIG. 16 is a perspective view showing a clamp of the blood collecting device shown in FIG. 15 according to (the fourth embodiment of) the present invention.
Figure 17:
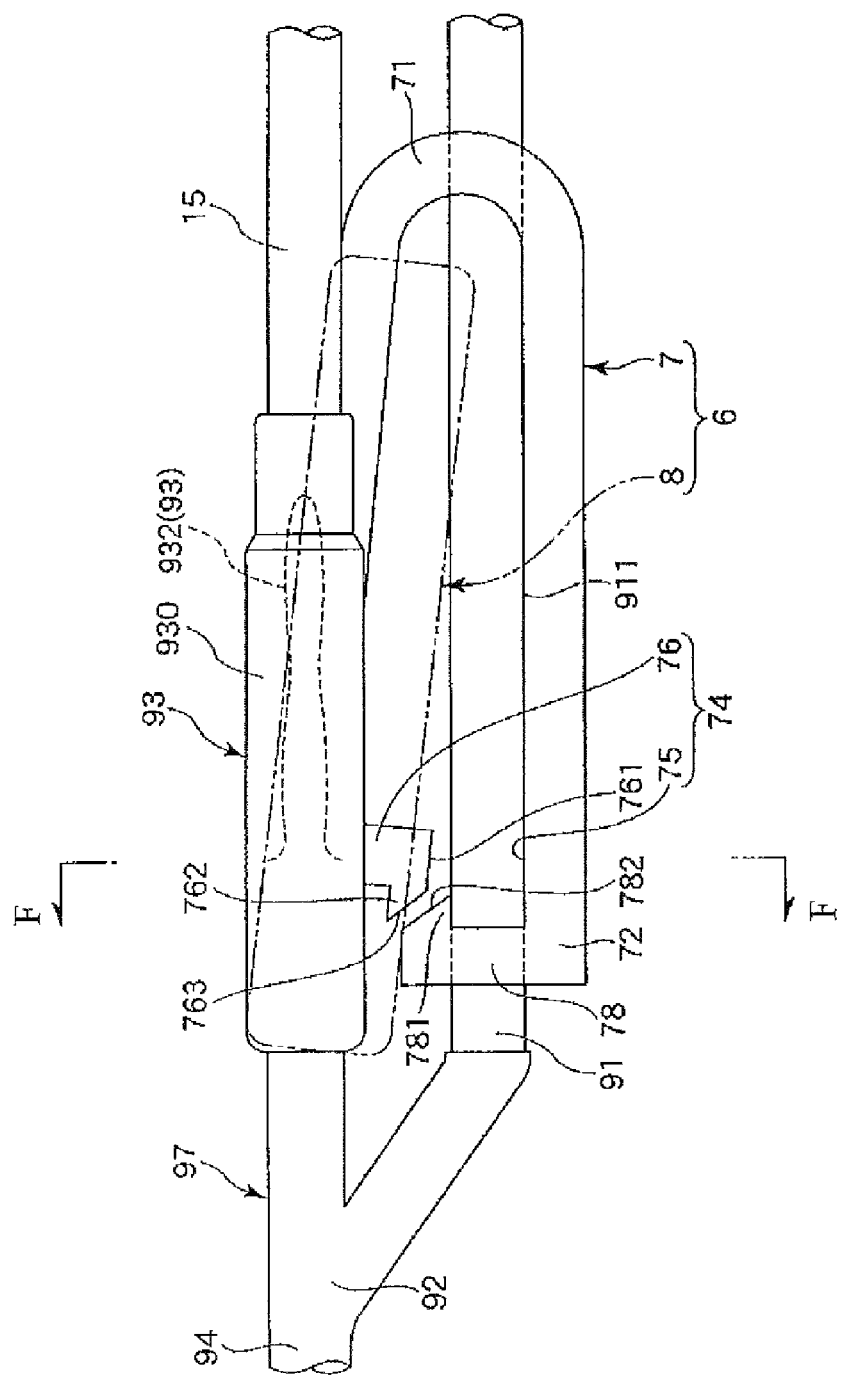
FIG. 17 is a schematic view of the clamp shown in FIG. 16 as viewed in a direction of an arrow E (a side view showing a first state of the clamp shown in FIG. 16)
Figure 18:
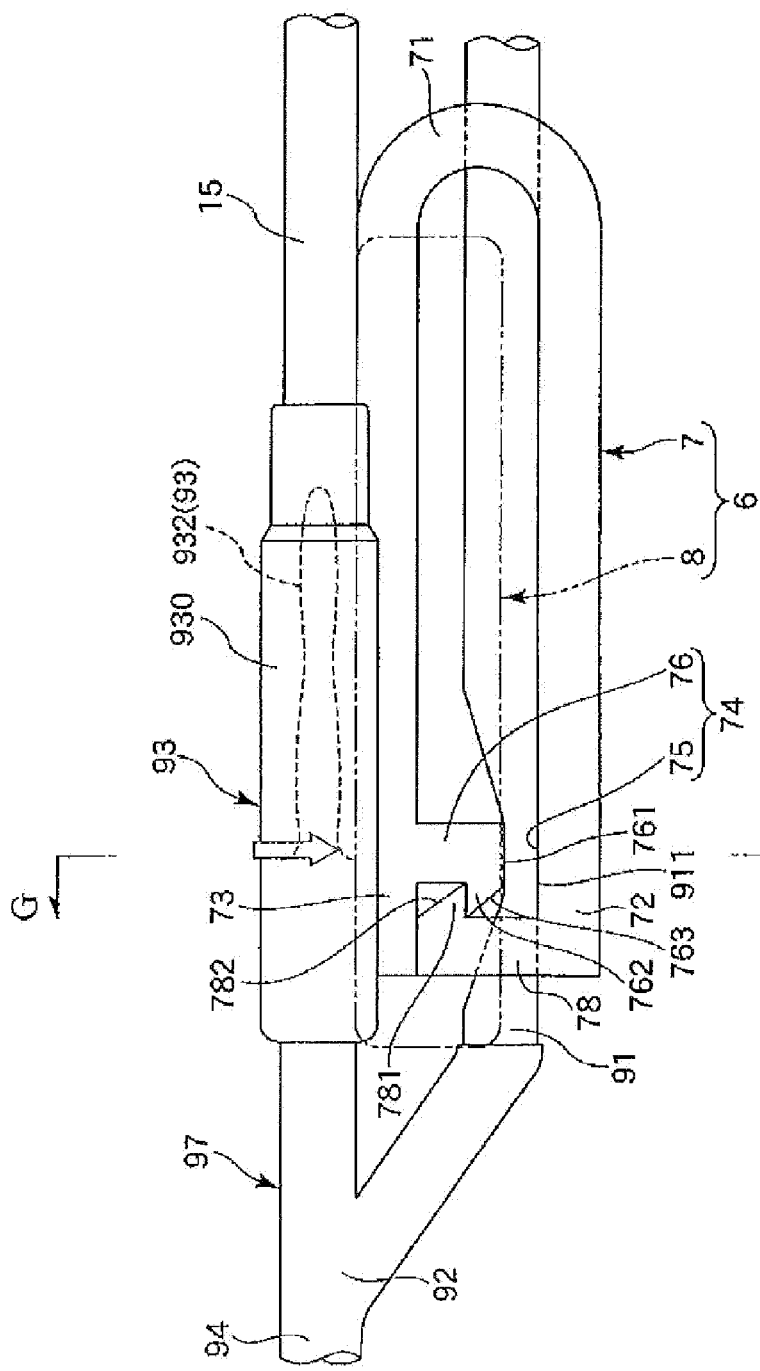
FIG. 18 is a schematic view of the clamp shown in FIG. 16 as viewed in the direction of the arrow E (a side view showing a second state of the clamp shown in FIG. 16)
Figure 19:
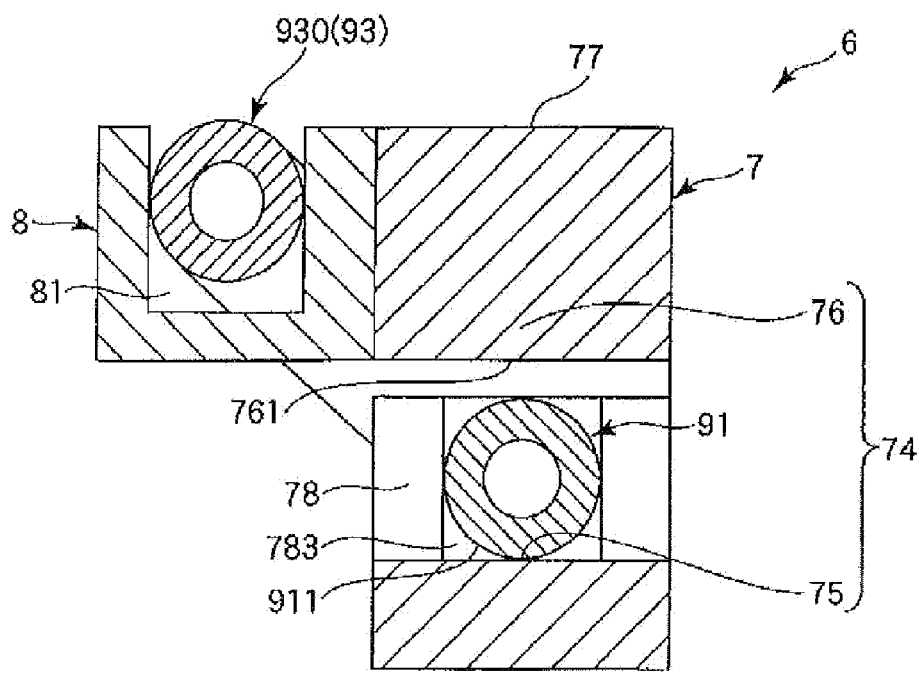
FIG. 19 is a cross-sectional view of the clamp cut along a line F-F in FIG. 17.
Figure 20:
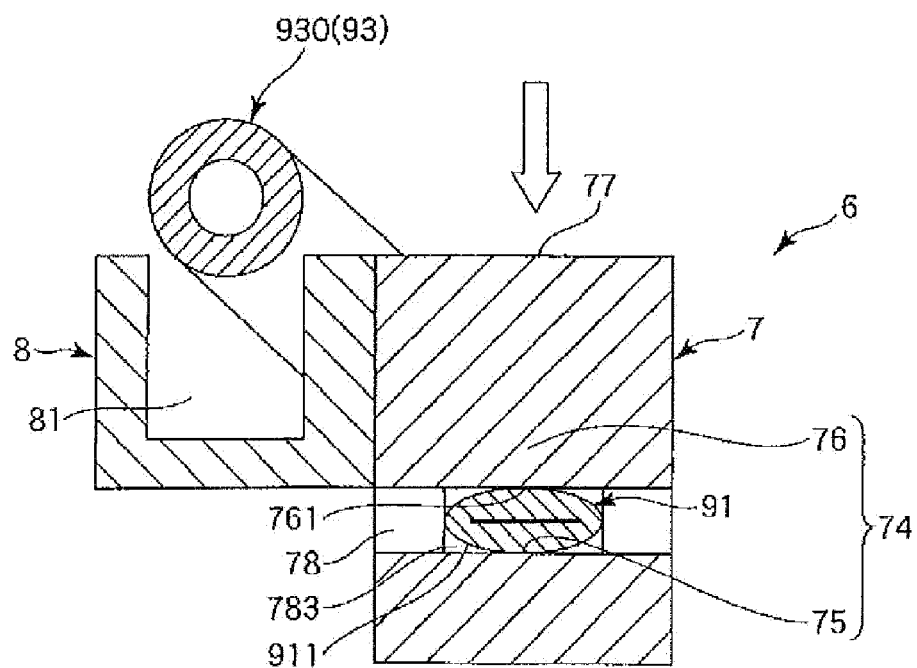
FIG. 20 is a cross-sectional view of the clamp cut along a line G-G in FIG. 18.

FIG. 15 is a schematic view (a plan view) showing a blood collecting device according to a fourth embodiment of the present invention. FIG. 16 is a perspective view showing a clamp of the blood collecting device shown in FIG. 15 according to (the fourth embodiment of) the present invention. FIGS. 17 and 18 are each a diagram showing the clamp shown in FIG. 16 as viewed from a direction of an arrow E (FIG. 17 is a side view showing a first state of the clamp shown in FIG. 16, and FIG. 18 is a side view showing a second state of the clamp shown in FIG. 16). FIG. 19 is a cross-sectional view taken along a line F-F in FIG. 17, and FIG. 20 is a cross-sectional view taken along a line G-G in FIG. 18. In the following explanation, in order to simplify the explanation, respective up sides of FIGS. 16 to 20 (the same is true of FIGS. 21 to 24) are defined as "up" and "upward" and respective lower sides thereof are defined as "down" and "downward".

An explanation will be given of the clamp and the blood collecting device according to the fourth embodiment of the present invention with reference to those figures, but the difference from the foregoing embodiment will be mainly explained and the explanation for the same matter will be omitted.

This embodiment is the same as the first embodiment except the structure of the clamp that is different.

As shown in FIG. 15, this embodiment has a clamp 6 provided in the vicinity of the branched portion 92.

As shown in FIG. 16, the clamp 6 includes two members: a press closing member (a coupling member) 7 that is also a main body (a clamp main body); and a preventing member (an preventing portion) 8. The clamp 6 has the press closing member 7 and the preventing member 8 coupled and fixed together, has the first state (an initial state) shown in FIG. 17 and the second state shown in FIG. 18 and transitions from the first state to the second state. The transition from the first state to the second state is carried out by pressing and operating the press closing member 7 (an operation portion 77). The structure of each component will be explained below.

The material of the press closing member 7 and the preventing member 8 is not limited to any particular one, and examples of such a material are various kinds of resin, such as polyvinyl chloride, polyethylene, polypropylene, cyclic polyolefin, polystyrene, poly-(4-methylpentene-1), polycarbonate, an acrylic resin, an acrylonitrile-butadiene-styrene copolymer, polyester like polyethylene-terephthalate and polyethylene-naphthalate, butadiene-styrene copolymer, and polyamide (e.g., nylon 6, nylon 6.6, nylon 6.10, and nylon 12). Among those, from the standpoint of easiness for molding, such resins as polypropylene, cyclic polyolefin, and polyester are preferable.

The clamp 6 is configured by the press closing member 7 and the preventing member 8 which are separate pieces coupled together in this embodiment, but the present invention is not limited to this structure. The press closing member 7 and the preventing member 8 may be formed integrally with each other.

As shown in FIGS. 16 to 18, the press closing member 7 is in a plate shape, and is a plate member which is curved (or bent) in the halfway of the lengthwise direction thereof. That is, the press closing member 7 is a plate member in a "U" (or "V") shape as viewed from a side. The second tube 91 is disposed inside the press closing member 7.

The press closing member 7 has a curved portion that serves as an elastic deformable portion 71 that is elastically deformable. Relative to one end (the bottom portion) 72 of the press closing member 7, another end (the upper portion) 73 thereof can be pressed against an elastic force of the elastic deformable portion 71 (see FIGS. 17 and 18). Therefore, an outer surface of another end 73 of the press closing member 7 functions as the operation portion 77 pressed and operated. It is preferable that the operation portion 77 should be provided with many grooves 771. Accordingly, when the operation portion 77 is pressed and operated by a finger, it is possible to prevent that finger from slipping from the operation portion 77, and thus a pressing operation is ensured.

The press closing member 7 is provided with a press closing portion (a pinching portion) 74 that can press and close the second tube 91. The press closing portion 74 includes an abutting portion 75 provided at one end 72 of the press closing member 7 (the coupling member), and a pressing portion 76 provided opposite to the abutting portion 75 at another end 73.

The abutting portion 75 is disposed onto a part of an outer circumference 911 of the second tube 91. The abutting portion 75 is defined by an internal plane of the one end 72 of the press closing member 7.

The pressing portion 76 is a portion (a protrusion) formed so as to protrude from the internal plane of another end 73 of the press closing member 7. This pressing portion 76 is disposed opposite the abutting portion 75 via the second tube 91.

In the first state shown in FIG. 17 (and FIG. 19), the pressing portion 76 is disposed apart from the second tube 91. In this state, the second tube 91 is opened from the upstream side to the downstream side, so that an initially flowing out blood passing through the tube 94 can flow in the initially flowing out blood bag 20 through the second tube 91. At this time, since the block-off member 93 is not torn yet, the initially flowing out blood is prevented from passing through the tube 15 and flowing in the blood collecting bag 10 (see FIG. 17).

When the operation portion 77 is pressed and operated against the elastic force by the elastic deformable portion 71 with the clamp 6 in the first state, the clamp 6 becomes in the second state shown in FIG. 18 (and FIG. 20). When the clamp 6 is in the second state, the pressing portion 76 is located in the proximity (vicinity) of the abutting portion 75, and a top face (a pressing plane) 761 thereof presses the outer circumference 911 of the second tube 91. Accordingly, the middle portion of the second tube 91 is pressed and closed (blocked) without fail. In this state, blood passing through the tube 94 is prevented from flowing through the second tube 91 into the initially flowing out blood bag 20.

As shown in FIGS. 16 to 18, the pressing portion 76 protruding from the internal plane of another end 73 of the press closing member 7 is provided with a first hook 762 extending toward the tip (toward the branched portion 92). The tip of the first hook 762 is provided with an inclined face 763.

On the other hand, a protrusion 78 is provided in a standing manner on the internal plane of the one end 72 of the press closing member 7 at a location closer to a tip beyond the abutting portion 75. The protrusion 78 is provided with a second hook 781 protruding toward a basal-end side. The portion of the second hook 781 at the basal-end side is provided with an inclined face 782 that is inclined in the substantially same direction as that of the inclined surface 763 of the first hook 762.

When the operation portion 77 is pressed and operated from the first state shown in FIG. 17, the first hook 762 has the inclined face 763 which is disposed on and made to slide on the inclined face 782 of the second hook 781. When the operation portion 77 is further pressed and operated, the first hook 762 goes over the second hook 781. At this time, the clamp 6 becomes in the second state. When the pressing action on the operation portion 77 is stopped, the top face 761 of the pressing portion 76 receives a counterforce from the second tube 91. Accordingly, the first hook 762 and the second hook 781 engage with each other, and the second state is maintained, i.e., it becomes possible to surely prevent unintentional cancelation of the second state so that it becomes the first state again (see FIG. 18). According to the clamp 6, the first hook 762 and the second hook 781 can be deemed as locking means (state maintaining means) for maintaining the second state.

As shown in FIG. 16, the protrusion 78 has a through-hole 783 passing all the way therethrough in the thickness direction, and the elastic deformable portion 71 also has a through-hole 711 passing all the way therethrough in the thickness direction. The second tube 911 runs through the through-holes 783 and 711. Accordingly, the second tube 91 is prevented from being detached from the press closing member 7, and thus the second tube 91 can be pressed and closed without fail by the press closing member 74 when the operation portion 77 is pressed.

As shown in FIG. 16, the clamp 6 has the preventing member 8 disposed abutting on the press closing member 7. The preventing member 8 prevents a tearing operation to the block-off member 93 in the first state.

The preventing member 8 is a long hollow member, and a hollow 81 thereof is opened toward the upper direction (an opposite direction to a retraction direction). That is, the preventing member 8 is a long member having a horizontal cross-section in a rectangular shape with one side opened toward the upper direction. Such a preventing member 8 is disposed in parallel with the another-end portion of the press closing member 7, and is coupled and fixed together with that portion. The way to fix these is not limited to any particular technique, and for example, a technique through bonding (bonding by an adhesive or a solvent), a technique by fusing (e.g., thermal fusion, high frequency fusion, ultrasonic fusion), etc., can be applied.

As shown in FIGS. 17 and 19, when the clamp 6 is in the first state, the block-off member 93 is covered by the preventing member 8. That is, the block-off member 93 is located (inserted) inside the hollow 81 of the preventing member 8. Accordingly, the block-off member 93 is not holdable and a tearing operation to the block-off member 93 can be prevented without fail.

As shown in FIGS. 18 and 20, when the clamp 6 is in the second state, the preventing member 8 moves downwardly together with the pressing portion 76 of the press closing member 74 in accordance with a pressing operation to the operation portion 77. Accordingly, the preventing member 8 is retracted from the block-off member 93 and the block-off member 93 is exposed. Hence, the state in which a tearing operation with the preventing member 8 is prevented is cancelled and thus the block-off member 93 becomes holdable and the tearing operation is enabled.

Next, an explanation will be given of an action of the blood collecting device 1 (an operated state (used state) of the clamp 6).

As shown in FIG. 15, in the blood collecting device 1, firstly, the clamp 6 is in the first state. Then, the tube 94 of the first tube 97 and the second tube 91 are communicated with each other (see FIGS. 17 and 19). Also, the tube 15 of the first tube 97 is in a plugged (closed) state by the block-off member 93. According to such a blood collecting device 1, when the blood collecting needle 151 is stuck in a donor, blood from the tube 94 can flow into the second tube 91 through the branched portion 92.

Moreover, as explained above, since the block-off member 93 is covered by the preventing member 8, a tearing operation is disabled (see FIGS. 17 and 19).

The blood collecting bag 10 of the blood collecting device 1 and the initially flowing out blood bag 20 are positioned at respective locations lower than the portion where the blood collecting needle 151 is stuck.

Next, the cap 154 is taken out from the blood collecting needle 151 (see FIG. 15), the blood collecting needle 151 is stuck in a vein (a blood vessel), and when it is confirmed that the blood collecting needle 151 is stuck in a vein, the hub 153 is fixed to the donor in the vicinity of the location where the blood collecting needle is stuck by means of, for example, an adhesive tape. Likewise, it is preferable that the first tube 97 (the tube 94) should be fixed to the vicinity of the location where the blood collecting needle is stuck by means of an adhesive tape.

Through such operations, an initially flowing out blood (blood) flows in the second tube 91 through the blood collecting needle 151, the tube 94, and the branched portion 92, flows through the second tube 91, and is introduced into the storage portion 23 of the initially flowing out blood bag 20. In this case, since the flow path of the tube 15 is blocked by the block-off member 93, the blood flows in the second tube 91 from the tube 94 through the branched portion 92 without fail.

Before the blood is introduced, air in the tube 94 and the second tube 91 is discharged from those tubes, and is collected into the initially flowing out blood bag 20. Accordingly, the pressures inside the tube 94 and the second tube 91 and the volumes of the inner cavity of the tube 94 and that of the second tube 91 are maintained more or less constant. As a result application of an excessive load on blood cells can be suppressed, and thus it becomes possible to suppress production of hemolysis or the like in the blood. Moreover, no blood enters the block-off-member-93 side at the branched portion 92 and is left there.

When the liquid level of the initially flowing out blood in the storage portion 23 of the initially flowing out blood bag 20 reaches a target position in the initially flowing out blood bag 20, the operation portion 77 of the press closing member 7 of the clamp 6 is pressed and operated in order to set the clamp 6 to be in the second state. Accordingly, the flow path of the second tube 91 becomes a closed state (see FIGS. 18 and 20).

Thus the blood collecting device 1 collects (obtains) a predetermined amount (a target amount) of blood in the initially flowing out blood bag 20. Through the initially flowing out blood collecting operation, an initially flowing out blood that may be contaminated by bacteria in some cases can be collected (eliminated) from the blood collected from the donor, so that the bacteria is prevented from mixing in the blood collected in the blood collecting bag 10 to be discussed later, thereby improving the safeness of a blood product.

Moreover, as explained above, when the clamp 6 is in the second state, the preventing member 8 is retracted from the block-off member 93, the block-off member 93 is exposed. Accordingly the tearing operation to the block-off member 93 is enabled (see FIGS. 18 and 20).

Furthermore, it is preferable that the second tube 91 should be pressed and closed before the tearing operation to the block-off member 93 is enabled when the clamp 6 becomes the second state from the first state. That is, when the clamp 6 is in the transition from the first state to the second state, it is preferable that the second tube 91 should be completely pressed and closed while the block-off member 93 should not be completely exposed (about to be completely exposed). Such a condition can be realized by setting, for example, the size (the shape) of the preventing member 8 appropriately.

Next, blood collection (real blood collection) into the blood collecting bag 10 is started.

In this case, the tearable portion 933 of the exposed block-off member 93 is torn in order to separate the solid column 932, thereby opening the flow path in the block-off member 93. Through this operation, the flow path of the first tube 97 is opened and the upstream side portion is communicated (opened) with the downstream side portion. Accordingly, the collected blood flows through the first tube 97, and is introduced into the blood storing portion 13 of the blood collecting bag 10. Therefore, the blood collecting bag 10 storing the blood excluding the initially flowing out blood (collected) is obtained.

While the blood is being collected into the blood collecting bag 10, the pressure-reduction blood collecting tube is inserted in the sampling port 29 of the initially flowing out blood bag 20, and the blood stored in the initially flowing out blood bag 20 is collected (sampling) in the pressure-reduction blood collecting tube. Thereafter, the pressure-reduction blood collecting tube which has collected the blood is removed from the sampling port 29. When the blood is sampled into a plurality of pressure-reduction blood collecting tubes, this operation is repeated.

Such sampling may be performed after the blood collection into the blood collecting bag 10 completes.

In the blood collection into the blood collecting bag 10, after a predetermined amount of blood is collected in the blood collecting bag 10, the blood collecting needle 151 is taken out from the blood vessel of the donor, and the first tube 97 and the second tube 91 are closed by fusing using a tube sealer if need be. Thereafter, the initially flowing out bag 20 and the blood collecting needle 151 are taken out.

Moreover, the blood stored (collected) in the blood collecting bag 10 is made to pass through a white-blood-cell removing filter in order to separate white blood cells and blood platelets, the remaining blood components are collected in a collecting bag, and the blood collecting bag 10 and the white-blood-cell removing filter are taken out. Thereafter, the blood in the collecting bag undergoes a centrifugal separation, is separated into red-blood-cell layers and blood plasma layers, and after the blood plasma is transferred into a blood plasma bag, a red-blood-cell preservation liquid in the bag filled with the red-blood-cell preservation liquid is added to the concentrated red blood cells left in the collecting bag, and is mixed therewith.

On the other hand, the initially flowing out collected in the pressure-reduction blood collecting tube is used for examinations, such as a biochemical examination of blood serum, and a nucleic acid amplification examination of infective viruses (e.g., AIDS virus, and hepatitis virus).

As explained above, according to the blood collecting device 1 (the clamp 6), when real blood collection is carried out after the initially flowing out is collected, the block-off member 93 provided in the first tube 97 becomes tearable after the second tube 91 is closed. That is, when the blood collecting device 1 is operated, it is possible to prevent without fail the block-off member 93 provided in the first tube 97 from being torn and the first tube 97 from being opened (communicated) with the upstream side portion in communication with the downstream side portion before the second tube 91 is closed.

If the block-off member 93 is torn before the second tube 91 is closed, the initially flowing out flows into the blood collecting bag 10 used for real blood collection even though the initially flowing out collecting operation completes. Then if the real blood collection gets started after this operation, the blood is contaminated by the initially flowing out already stored in the blood collecting bag 10 and all collected blood must be disposed (the blood is wasted).

According to the blood collecting device 1 (the clamp 6), however, such a failure can be surely prevented.

Fifth Embodiment

Figure 21:
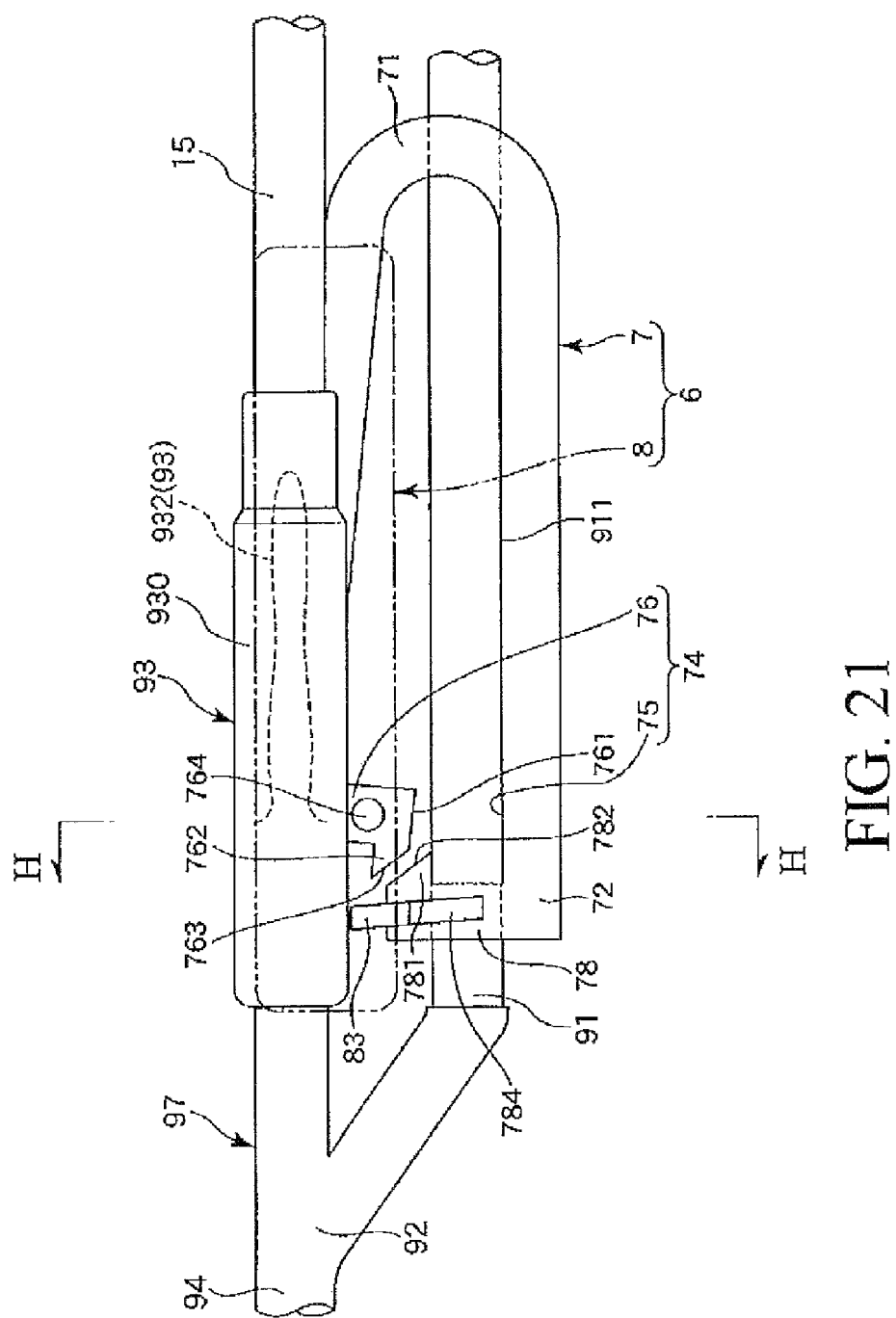
FIG. 21 is a side view of a clamp in a first state according to (a fifth embodiment of) the present invention.
Figure 22:
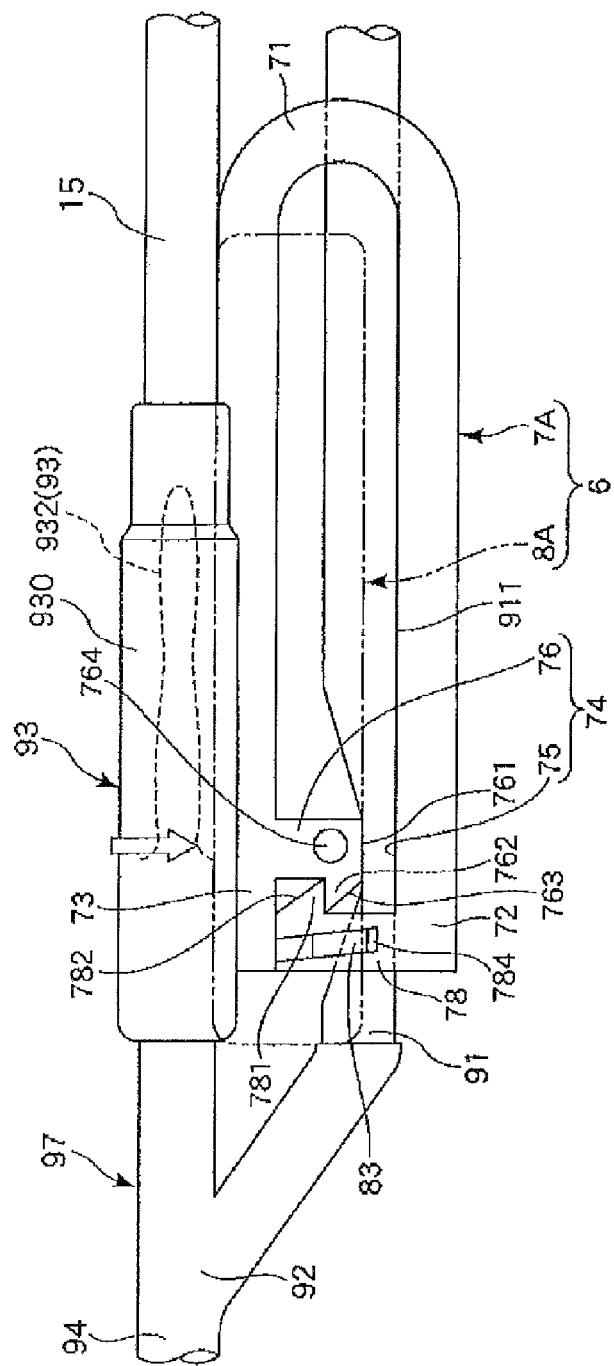
FIG. 22 is a side view of the clamp in a second state according to (the fifth embodiment of) the present invention.
Figure 23:
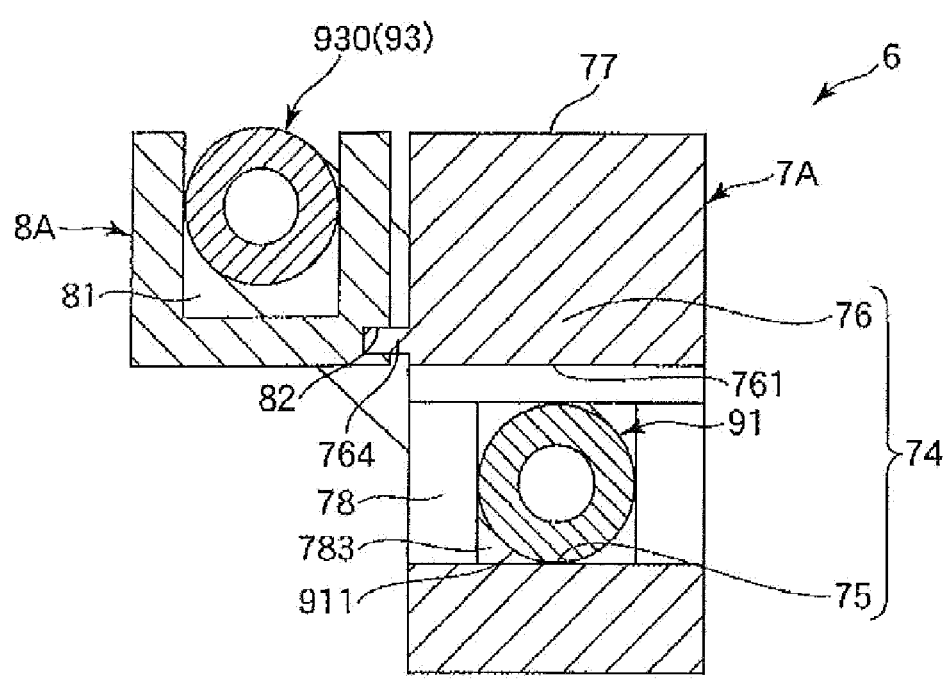
FIG. 23 is a cross-sectional view of the clamp cut along a line H-H in FIG. 21.

FIG. 21 is a side view showing a first state of a clamp according to (a fifth embodiment of) the present invention. FIG. 22 is a side view showing a second state of the clamp according to (the fifth embodiment of) the present invention. FIG. 23 is a cross-sectional view taken along a line H-H in FIG. 21.

An explanation will be given of the clamp and a blood collecting device according to the fifth embodiment of the present invention with reference to those figures, but the difference from the foregoing embodiment will be mainly explained and the explanation for the same matter will be omitted.

This embodiment is the same as the fourth embodiment except a coupling state of a press closing member and a preventing member that is different.

As shown in FIGS. 21 to 23, a press closing member 7A and a preventing member 8A are coupled together in a rotatable manner.

The pressing portion 76 of the press closing member 7A has an axis (a rotation axis) 764 (see FIG. 23) that is formed to protrude from a side face of the pressing portion at the preventing-member-8A side. On the other hand, the preventing member 8A has an axis bearing portion 82 (see FIG. 23) which is a recess formed on a side face f the press closing-member-7A and which receives the shaft 764. The preventing member 8A is rotatable relative to the press closing member 7A with the axis 764 and the axis bearing portion 82.

Instead of the axis 764 and the axis bearing portion 82, the press closing member 7A and the preventing member 8A may be coupled with a pin that penetrates through these members may be provided.

A cam groove 784 (see FIGS. 21 and 22) is formed in the protrusion 78 of the press closing member 7A. A follower portion 83 which is inserted in the cam groove 784 and serves as a cam-follower is protrudingly formed on the preventing member 8A.

The cam groove 784 and the follower portion 83 allow the preventing member 8A to maintain a posture (hereinafter, this posture will be referred to as a "parallel posture") so as to be parallel to the tube 15 of the first tube 97 in the first state as shown in FIG. 21. Accordingly, not only a portion of the tube 15 where the block-off member 93 is provided but also the other portions thereof back and forth are covered by the preventing member 8A, so that a tearing operation to the block-off member 93 is surely prevented.

When the operation portion 77 is pressed and operated, the preventing member 8A has the follower portion 83 guided by the cam groove 784 of the press closing member 7A, and moves downwardly while maintaining the parallel posture, i.e., moves in a parallel manner. As shown in FIG. 22, in the second state after the movement, the preventing member 8A maintains the parallel posture. Accordingly, the whole tube 15 is exposed and a tearing operation to the block-off member 93 is enabled.

As explained above, it can be deemed that the cam groove 784 and the follower portion 83 configure posture maintaining means for allowing the preventing member 8A to maintain a posture relative to the tube 15.

Sixth Embodiment

Figure 24:
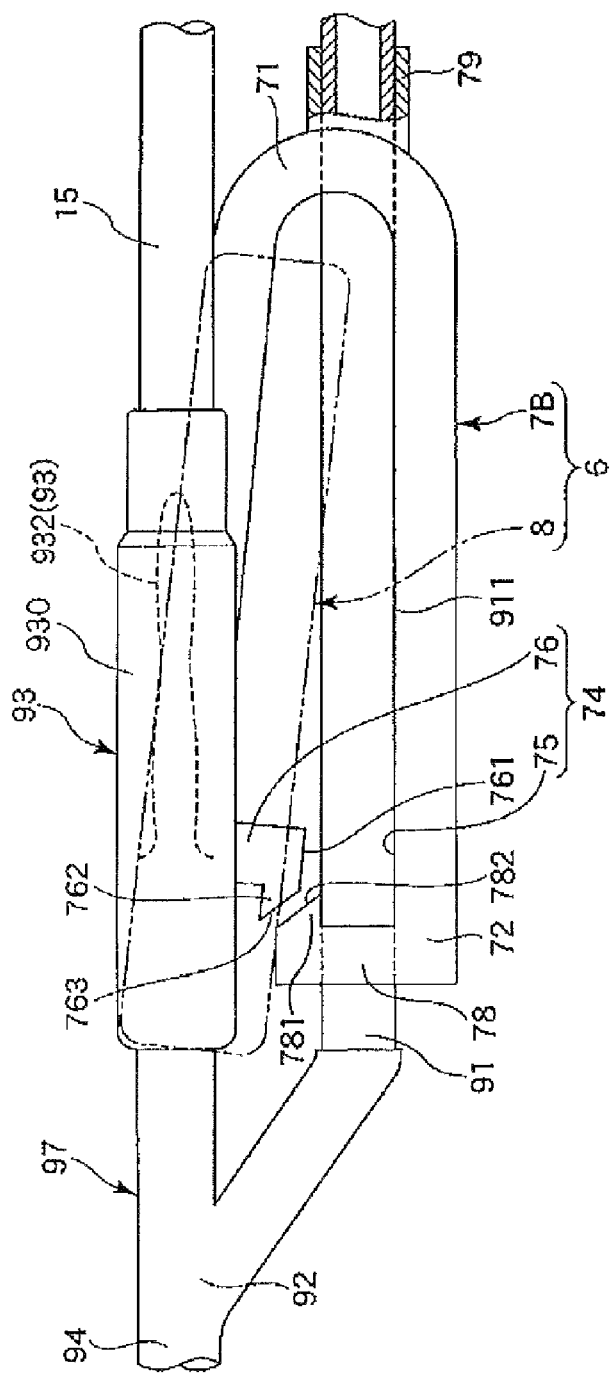
FIG. 24 is a partial vertical cross-sectional side view showing a first state of a clamp according to (a sixth embodiment of) the present invention.

FIG. 24 is a partial vertical cross-sectional side view showing a first state of a clamp according to (a sixth embodiment of) the present invention.

An explanation will be given of the clamp and a blood collecting device according to the sixth embodiment of the present invention with reference to this figure, but the difference from the foregoing embodiment will be mainly explained and the explanation for the same matter will be omitted.

This embodiment is same as the fourth embodiment other than fixing means.

As shown in FIG. 24, a press closing member 7B has a fitting portion 79 which is provided at a basal end and which serves as fixing means for fixing the second tube 91. The fitting portion 79 is in a tubular shape, and has a slightly smaller internal diameter than the outer diameter of the second tube 91. The middle portion of the second tube 91 is fitted in the fitting portion 79. Accordingly, the second tube 91 (and also the first tube 97) is surely fixed. That is, positioning is carried out which surely prevents the clamp 6 from being unintentionally displaced in the lengthwise direction of the tube.

Although the fixing means for fixing the second tube 91 is the fitting portion 79 in this embodiment, the present invent is not limited to this structure. For example, the fixing means may be an adhesive that bonds the one end 72 of the press closing member 7B with the second tube 91, and the one end 72 of the press closing member 7B may be provided with a fitting portion with the branched portion 92.

The fixing means is not limited to ones that fix the second tube 91, and for example, it may be means for fixing the first tube 97 (the tube 91), or may be means for fixing both first tube 97 and second tube 91.

Although embodiments of the clamp and blood collecting device of the present invention were explained above with reference to the drawings, the present invention is not limited to the above-explained embodiments. Each component configuring the clamp and the blood collecting device may be replaced with an equivalent that can attain the same function. Also, an arbitrary component may be additionally provided.

The clamp and the blood collecting device of the present invention can employ a combined structure (feature) of equal to or greater than two arbitrary structures of respective embodiments.

According to the structure shown in FIGS. 1 and 15, the second tube of the blood collecting device runs (is branched) in an upper right tilting direction relative to the first tube, but the present invention is not limited to this structure. The second tube may run in any direction relative to the first tube. In this case, in the cases of the first to third embodiments, it is preferable to set the position of the second press closing portion of the second plate member and that of the preventing portion as needed depending on the running direction of the second tube.

Also, in the cases of the first to third embodiments, it is preferable that the clamp should have preventing means for preventing a state change from the second state to the first state. That is, it is preferable that the clamp should have an irreversibility.

According to the illustrated structures of the fourth to sixth embodiments, the press closing portion has the abutting portion and the pressing portion and the pressing portion protrudes toward the abutting portion. The present invention is, however, not limited to this structure and the abutting portion may protrude toward the pressing portion.

Also, according to the illustrated structures of the fourth to sixth embodiments, a hook (an engaging portion) that serves as position restriction means for restricting the position of the first tube 97 relative to the tube 15 may be provided at one end of the press closing member. Accordingly, it is possible to prevent the block-off member 93 from being retracted from the preventing member 8 in the first state.

INDUSTRIAL APPLICABILITY

The clamp of the present invention is provided in a blood collecting device that includes a first tube having one end and another end connected to a blood collecting needle and a blood bag, respectively, a second tube branched from a halfway of the first tube through a branched portion, and a block-off member which is provided in the first tube at the blood-bag side beyond the branched portion and which allows the first tube in a blocked state to be opened when torn, in which the clamp is arranged at the branched portion, and is configured to change a state between a first state in which the second tube is opened and a tearing operation to the block-off member is disabled, and a second state in which the second tube is closed and a tearing operation to the block-off member is enabled. Accordingly, when the blood collecting device is operated, it is possible to surely prevent the first tube in the blood collecting device from being opened before the second tube branched from the first tube is closed. Hence, the clamp of the present invention has an industrial applicability.

The invention claimed is:

1. A blood collecting device comprising:
a first tube having one end and another end connected to a blood collecting needle and a blood bag, respectively;
a second tube branched from an intermediate portion of the first tube through a branched portion;
a block-off member which is provided in the first tube at the blood-bag side beyond the branched portion and which allows the first tube in a blocked state to be opened when torn; and
a clamp being disposed at the branched portion and being positionable in a first state in which the second tube is opened and a tearing operation to the block-off member is disabled and a second state in which the second tube is closed and a tearing operation to the block-off member is enabled, the clamp being configured to change positions from the first state to the second state.

2. The blood collecting device according to claim 1, wherein the clamp further comprises a clamp main body and an operation member rotatable relative to the clamp main body, the operation member comprising a pressing portion that presses and closes the second tube and a preventing portion that prevents a tearing operation to the block-off member; and
wherein when the operation member is operated to rotate relative to the clamp main body, the blood collecting device becomes in the second state from the first state.

3. The blood collecting device according to claim 1, wherein when the position of clamp of the blood collecting device is changed to the second state from the first state, the second tube is closed before the tearing operation is enabled.

4. The blood collecting device according to claim 2, wherein the preventing portion covers a part of the first tube where the block-off member is provided in the first state, and is retracted from the covering part in the second state.

5. The blood collecting device according to claim 4, wherein the operation member is a plate member; and
the preventing portion is a protrusion protruding from an outer circumference of the operation member toward an exterior.

6. The blood collecting device according to claim 4, wherein the clamp main body is a plate member and is provided with a notch in an outer circumference thereof which is a cut-out of a portion corresponding to the block-off member;
the operation member is a plate member; and
the preventing portion comprises a portion of the outer circumference of the operation member facing the notch in the first state.

7. The blood collecting device according to claim 2, wherein the pressing portion includes an inclined portion which is apart from the clamp main body and which gradually reduces a distance therefrom when the operation member is operated to rotate.

8. The blood collecting device according to claim 2, wherein the clamp main body includes a fixing portion that fixes the branched portion.

9. The blood collecting device according to claim 2, wherein the operation member includes an operation lever that is caught by a finger when the operation member is operated to rotate.

10. The blood collecting device according to claim 2, wherein the clamp further comprises restriction means for restricting a rotatable range of the operation member.

11. The blood collecting device according to claim 1, wherein the clamp further comprises a clamp main body and a preventing portion which is coupled to the clamp main body and which prevents a tearing operation to the block-off member;
wherein the clamp main body includes a pinching portion which presses and closes the second tube, and an operation portion for operating the pinching portion; and
when the operation portion is operated, the clamp position is changed from the first state to the second state.

12. The blood collecting device according to claim 11, wherein when the clamp is positioned in the first state, the preventing portion covers a part of the first tube where the block-off member is provided and when the clamp is positioned in the second state, the preventing portion is retracted from the covering part.

13. The blood collecting device according to claim 2, wherein the preventing portion is a long hollow member having a hollow opened in a direction opposite to a direction in which the preventing portion retracts.

14. The blood collecting device according to claim 11, wherein the pinching portion includes:
   an abutting portion that abuts a part of an outer circumference of the second tube; and
   a pressing portion which is provided so as to face the abutting portion via the second tube, and which comes close to the abutting portion through the pressing operation, and presses the outer circumference of the second tube.

15. The blood collecting device according to claim 11, wherein the preventing portion comprises a long hollow member with a hollow; and
   the clamp main body and the hollow member are arranged adjacent to each other and in parallel with each other.

16. The blood collecting device according to claim 15, wherein the hollow member is coupled to the clamp main body in a rotatable manner relative to the clamp main body.

17. The blood collecting device according to claim 11, wherein the clamp further comprises fixing means for fixing at least either one of the first tube and the second tube.

* * * * *